(12) United States Patent
Wang et al.

(10) Patent No.: US 12,017,015 B2
(45) Date of Patent: Jun. 25, 2024

(54) URETHRAL CATHETERIZATION SYSTEM, URINARY CATHETER CONVEYING DEVICE THEREOF, AND METHOD OF USING THE SAME

(71) Applicants: Chung-Cheng Wang, New Taipei (TW); Ming-Chien Chiu, New Taipei (TW)

(72) Inventors: Chung-Cheng Wang, New Taipel (TW); Yung-Ping Wang, New Taepei (TW); Yi-Yuan Chen, New Taipei (TW); Chia-Ming Hsu, Taipei (TW)

(73) Assignees: Chung-Cheng Wang, New Taipei (TW); Ming-Chien Chiu, New Taipei (TW)

( * ) Notice: Subject to any disclaimer, the term of this patent is extended or adjusted under 35 U.S.C. 154(b) by 0 days.

(21) Appl. No.: 17/830,845

(22) Filed: Jun. 2, 2022

(65) Prior Publication Data
US 2022/0387756 A1    Dec. 8, 2022

(30) Foreign Application Priority Data
Jun. 7, 2021  (TW) ................................. 110206551

(51) Int. Cl.
*A61M 25/00*  (2006.01)
*A61M 25/01*  (2006.01)
*A61M 25/02*  (2006.01)

(52) U.S. Cl.
CPC . *A61M 25/0113* (2013.01); *A61M 2025/0001* (2013.01); *A61M 25/0105* (2013.01);
(Continued)

(58) Field of Classification Search
CPC ...... A61M 25/0113; A61M 2025/0001; A61M 2025/026; A61M 25/0155; A61M 25/0105
See application file for complete search history.

(56) References Cited

U.S. PATENT DOCUMENTS

| 2011/0166513 A1* | 7/2011 | Cohen .................... A61B 34/30 |
| | | 604/95.01 |
| 2017/0239011 A1* | 8/2017 | Lucas ............... A61M 16/0875 |

(Continued)

FOREIGN PATENT DOCUMENTS

CN    111467117 A  *  7/2020  ............. E04B 1/342

OTHER PUBLICATIONS

"Mounted". 2023. In Oxford Learner's Dictionaries.com. Retrieved Oct. 31, 2023 from https://www.oxfordlearnersdictionaries.com/us/definition/english/mounted?q=mounted (Year: 2023).*

*Primary Examiner* — Andrew J Mensh
*Assistant Examiner* — Leah Jenna Anne Sibay
(74) *Attorney, Agent, or Firm* — Faegre Drinker Biddle & Reath LLP

(57) ABSTRACT

A urinary catheter conveying device includes a sleeve member, a conveying assembly and a controller. The sleeve member is for sleeving onto a glans of a penis and has a guiding hole to be registered with an external urethral orifice of the glans. The conveying assembly includes a casing removably mounted to the sleeve member, and a conveying mechanism for advancing the urinary catheter to the guiding hole such that the urinary catheter is inserted into the external urethral orifice. The controller controls the conveying mechanism to advance the urinary catheter to the guiding hole. A urinary catheterization system and a method of using the urinary catheterization system are also disclosed.

13 Claims, 21 Drawing Sheets

(52) U.S. Cl.
CPC ............... *A61M 2025/026* (2013.01); *A61M 2205/3327* (2013.01); *A61M 2205/583* (2013.01); *A61M 2205/587* (2013.01); *A61M 2205/8206* (2013.01); *A61M 2210/1096* (2013.01); *A61M 2210/167* (2013.01)

(56) References Cited

U.S. PATENT DOCUMENTS

2018/0140799 A1\* 5/2018 Herrera ................ A61B 5/205
2018/0326184 A1\* 11/2018 Sisco ................... A61M 25/02
2022/0401700 A1\* 12/2022 Shay .................... A61M 25/02

\* cited by examiner

URETHRAL CATHETERIZATION SYSTEM, URINARY CATHETER CONVEYING DEVICE THEREOF, AND METHOD OF USING THE SAME

CROSS-REFERENCE TO RELATED APPLICATION

This application claims priority to Taiwanese Utility Model Patent Application No. 110206551, filed on Jun. 7, 2021, the entire disclosure of which is hereby explicitly incorporated by reference herein.

FIELD

The disclosure relates to a urethral catheterization system, and more particularly to a urethral catheterization system, a urinary catheter conveying device thereof, and a method of using the same.

BACKGROUND

A urinary catheter is used for being inserted through a patient's urethra into the patient's bladder to help the patient drain his bladder. However, since the urinary catheter is flexible, when it is manually inserted into an external urethral orifice of a glans of a patient by a person, usually, a nursing staff, the nursing staff must have substantial experiences to achieve accurate insertion of the urinary catheter. Inaccurate or incorrect insertion of the urinary catheter may require repeated insertion into the glans, which can discomfort the patient. In addition, in some cases, a patient needs to insert the urinary catheter into his external urethral orifice by himself or by his family member when the patient is not at a medical institution. Therefore, there is a need to facilitate assembly of a urinary catheter onto a patient's penis.

SUMMARY

Therefore, an object of the disclosure is to provide a urinary catheter conveying device that can alleviate at least one of the drawbacks of the prior art.

According to the disclosure, the urinary catheter conveying device is adapted for guiding a urinary catheter to a penis, and includes a sleeve assembly, a conveying assembly and a controller. The sleeve assembly is adapted to be disposed on the penis, and includes a sleeve member that is adapted for sleeving onto a glans of the penis and that has a guiding hole adapted to be registered with an external urethral orifice of the glans. The conveying assembly includes a casing and a conveying mechanism. The casing is removably mounted to the sleeve member. The conveying mechanism is disposed in the casing, and is adapted for advancing the urinary catheter to the guiding hole such that the urinary catheter is inserted into the external urethral orifice through the guiding hole. The controller is electrically coupled to the conveying mechanism and is adapted for controlling the conveying mechanism to advance the urinary catheter to the guiding hole.

Another object of the disclosure is to provide a urinary catheterization system that can alleviate at least one of the drawbacks of the prior art.

According to the disclosure, the urinary catheterization system includes a urinary catheter and the urinary catheter conveying device as mentioned above.

Still another object of the disclosure is to provide a method of using a urinary catheterization system that can alleviate at least one of the drawbacks of the prior art.

According to the disclosure, the method for using the urinary catheterization system includes steps of: a) assembling a sleeve assembly onto a penis; b) assembling the sleeve assembly with a conveying assembly and a urinary catheter; c) controlling the conveying assembly to advance the urinary catheter to a guiding hole of a sleeve member of the sleeve assembly by a controller so that the urinary catheter is inserted into an external urethral orifice of a glans of the penis through the guiding hole.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
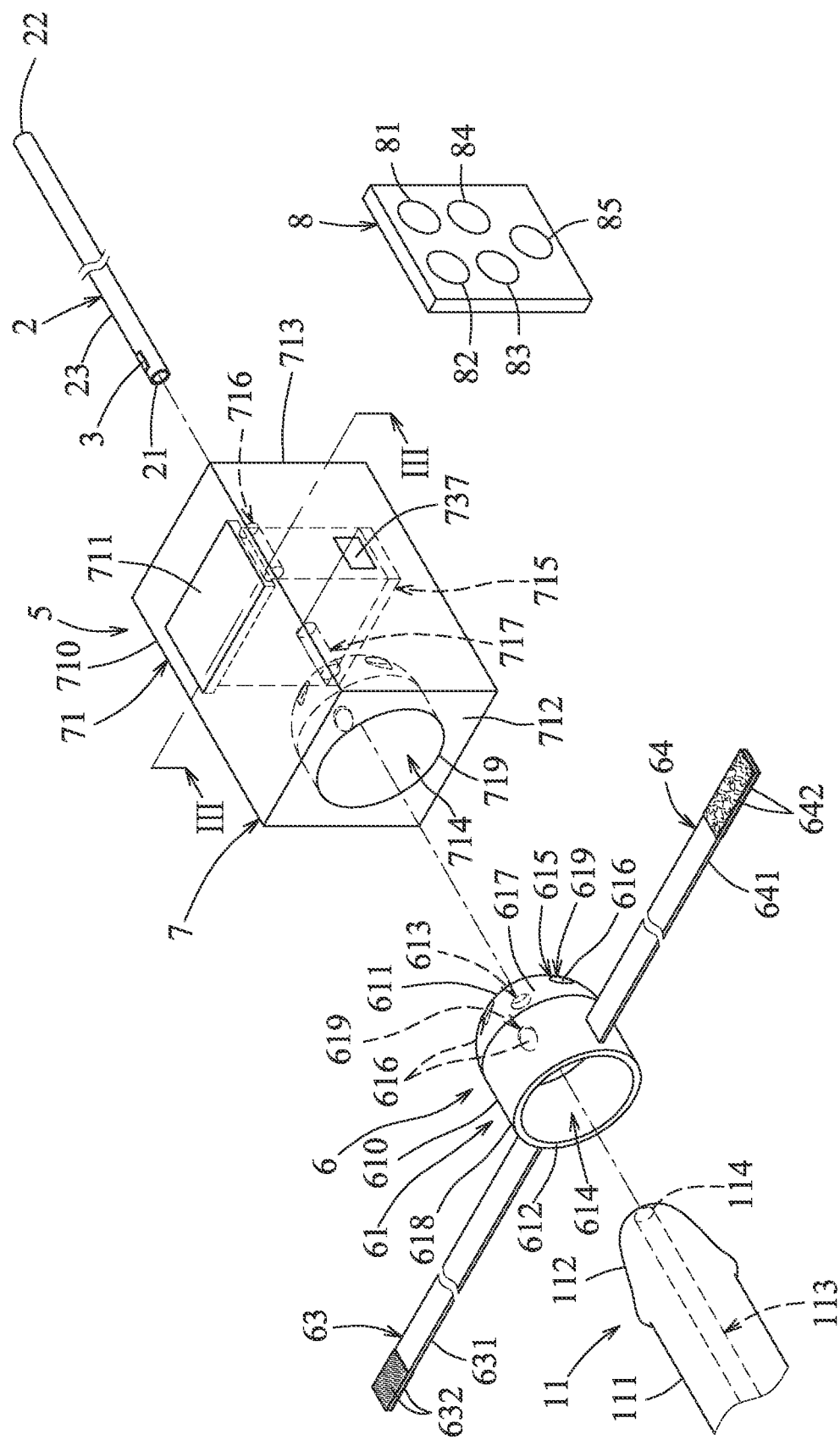
FIG. 1 is a fragmentary, partly exploded perspective view of a first embodiment of a urinary catheterization system according to the disclosure, and a fragmentary view of a penis.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, a first embodiment of a urinary catheterization system according to the disclosure is adapted to be assembled onto a penis 11. The penis 11 has a penis shaft 111, a glans 112 that is formed at an end of the penis shaft 111, an external urethral orifice 114 that is formed at one end of the glans 112 opposite to the penis shaft 111, and a urethra 113 that extends from the external urethral orifice 114 through the glans 112 and the penis shaft 111.

The first embodiment includes a urinary catheter 2, a pressure sensor 3 and a urinary catheter conveying device 5. The urinary catheter 2 may be made from a rubber material, or a silicone material, and has an inserting end 21, a rear end 22 opposite to the inserting end 21, and an outer catheter surface 23 between the inserting end 21 and the rear end 22. The inserting end 21 is adapted to be inserted into the external urethral orifice 114 of the glans 112. The rear end 22 is adapted to be connected to a urine collector (not shown) such as a urine bag.

The pressure sensor 3 is mounted to the outer catheter surface 23 of the urinary catheter 2, and is adjacent to the inserting end 21 of the urinary catheter 2. The pressure sensor 3 is used for detecting a pressure after the urinary catheter 2 is inserted through the external urethral orifice 114 into the urethra 113 of the penis 11. The pressure sensor 3 generates a first pressure signal when detecting a pressure whose value is larger than a preset value, and generates a second pressure signal when detecting that a first detected state, in which a pressure is detected, is switched to a second detected state, in which no pressure is detected.

Figure 2:
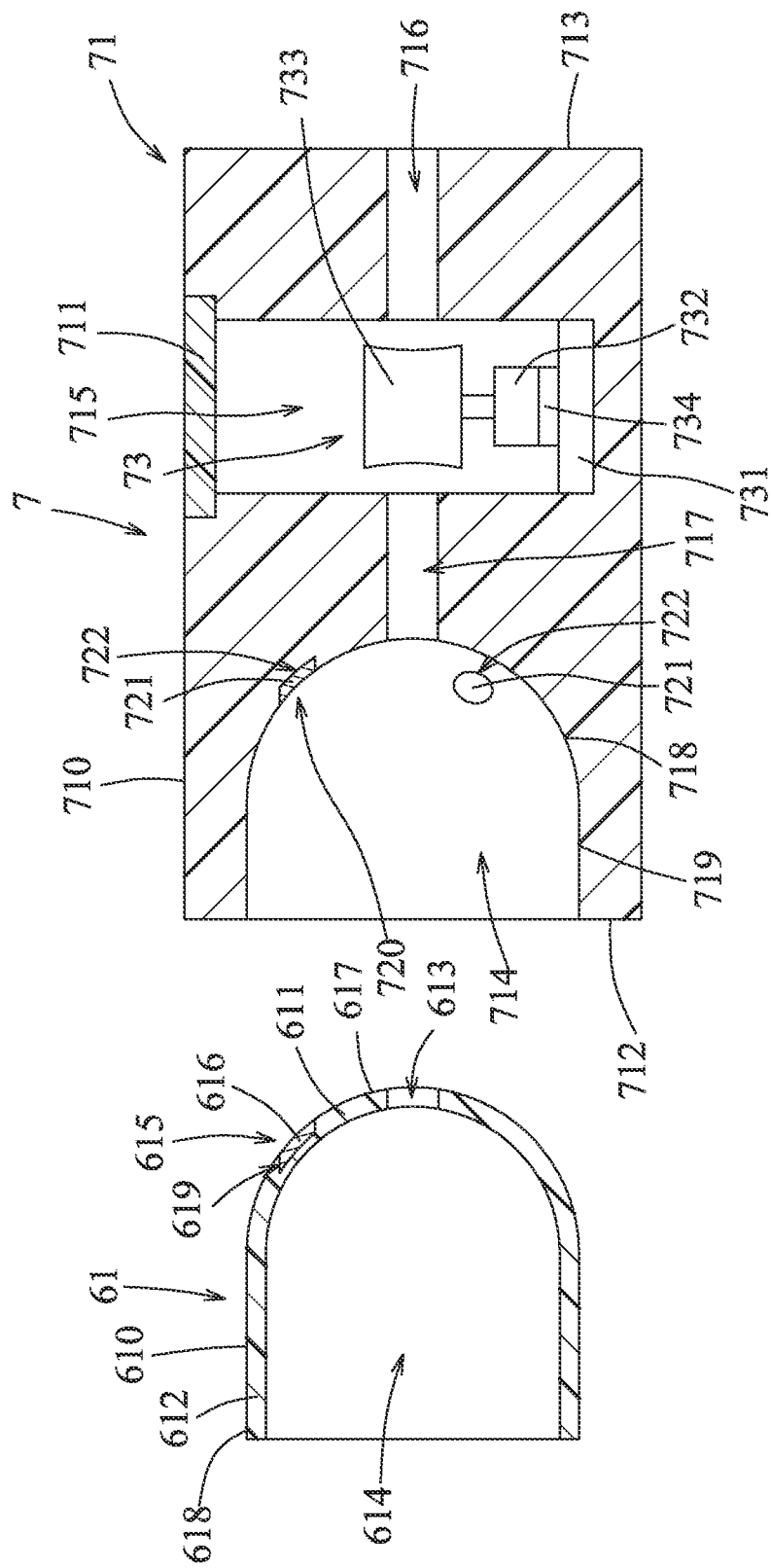
FIG. 2 is a sectional view of a sleeve assembly and a conveying assembly of the first embodiment.

Referring further to FIG. 2, the urinary catheter conveying device 5 is operable to guide the urinary catheter 2 to the penis 11, and includes a sleeve assembly 6, a conveying assembly 7 and a controller 8. The sleeve assembly 6 is configured to be portable, is adapted to be disposed on the penis 11, and includes a sleeve member 61, a first band 63 that is connected to the sleeve member 61, and a second band 64 that is spaced apart from the first band 63 and that is connected to the sleeve member 61. In this embodiment, the first and second bands 63, 64 are respectively connected to two opposite sides of the sleeve member 61. The sleeve member 61 is adapted for sleeving onto the glans 112 of the penis 11, is made from a resilient material, and includes a sleeve main body 610 that may be made from, but not limited to, a plastic material. The sleeve main body 610 has a dome-shaped (or hemispherical) cap portion 611, a tubular portion 612 that extends from one end of the dome-shaped cap portion 611 (i.e., the dome-shaped cap portion 611 is connected to one end of the tubular portion 612), and a guiding hole 613. The guiding hole 613 extends centrally through the dome-shaped cap portion 611, and is adapted to be registered with the external urethral orifice 114 of the glans 112. A cross section of the guiding hole 613 corresponds in shape to a cross section of the urinary catheter 2. In this embodiment, the guiding hole 613 is circular (i.e., the cross section of the guiding hole 613 is circular). The tubular portion 612 and the dome-shaped cap portion 611 cooperatively define an accommodating groove 614 that spatially communicates with the guiding hole 613 and that is adapted for accommodating the glans 112.

The sleeve member 61 further includes a sleeve connector unit 615 that is disposed on the sleeve main body 610. Specifically, the dome-shaped cap portion 611 and the tubular portion 612 of the sleeve main body 610 respectively have an outer dome-shaped surface 617 and an outer surrounding surface 618 that is connected to the outer dome-shaped surface 617. The sleeve main body 610 has a plurality of mounting grooves 619 that are recessed in the outer dome-shaped surface 617 and that are spaced apart from each other. In the first embodiment, the mounting grooves 619 are angularly spaced apart from each other, and the sleeve connector unit 615 includes a plurality of magnetic components 616 that are respectively bonded into the mounting grooves 619 and that are flush with the outer dome-shaped surface 617.

The first band 63 includes a band body 631 that is connected to the outer surrounding surface 618 of the tubular portion 612 of the sleeve main body 610, and two hook-surfaced components 632 that are respectively disposed on two opposite surfaces of the band body 631 thereof. The second band 64 includes a band body 641 that is connected to the outer surrounding surface 618 of the tubular portion 612, and two loop-surfaced components 642 that are respectively disposed on two opposite surfaces of the band body 641 thereof. The first and second bands 63, 64 are adapted to be wound and tied around the penis shaft 111 of the penis 11. Each of the loop-surfaced components 642 is removably stickable to a respective one of the hook-surfaced components 632. A user may adjust the winding length and tightness of the first and second bands 63, 64 around a penis shaft of the patient according to the girth and length of the penis shaft, and then fastens one of the loop-surfaced components 642 to the respective one of the hook-surfaced components 632 to tie the sleeve member 61 to the penis shaft. It is noted that, in certain embodiments, the first band 63 may include the loop-surfaced components 642 and the second band 64 may include the hook-surfaced components 632.

Figure 3:
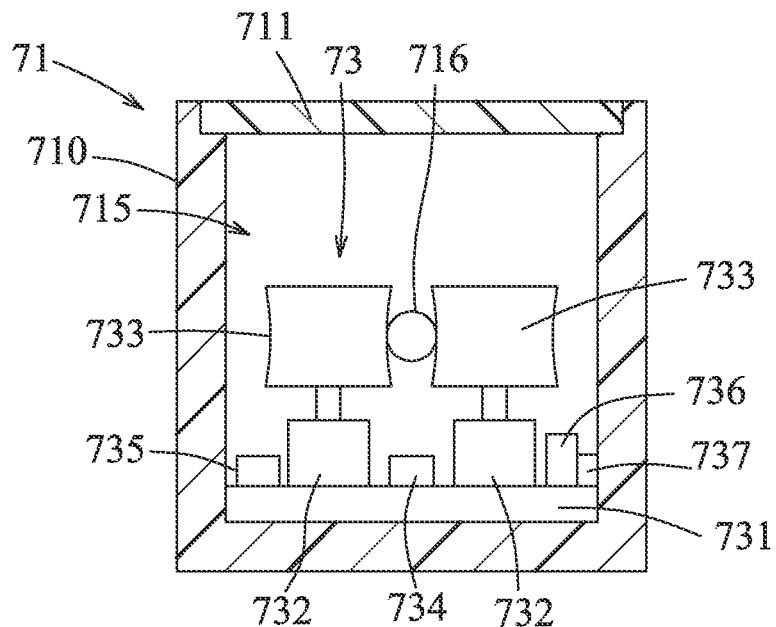
FIG. 3 is a sectional view taken along line III-III in FIG. 1.

Referring further to FIG. 3, the conveying assembly 7 is configured to be portable, and includes a casing 71 and a conveying mechanism 73 that is disposed in the casing 71. The casing 71 includes a casing body 710 that is removably mounted to the sleeve member 61, and a lid body 711. The casing body 710 has a front surface 712, a rear surface 713 opposite to the front surface 712, a positioning groove 714, an accommodating space 715, a first casing passage 716, a second casing passage 717, an inner surrounding surface 719 and an inner dome-shaped surface 718. The positioning groove 714 is recessed in the front surface 712 to receive and position the sleeve member 61 of the sleeve assembly 6. Specifically, the inner surrounding surface 719 abuts against the outer surrounding surface 618 of the tubular portion 612 of the sleeve member 61. The inner dome-shaped surface 718 interconnects the inner surrounding surface 719 and the front surface 712, abuts against the outer dome-shaped surface 617 of the dome-shaped cap portion 611 of the sleeve member 61, and cooperates with the inner surrounding surface 719 to define the positioning groove 714. The shape of the positioning groove 714 corresponds to that of the sleeve member 61 so that the sleeve member 61 is snugly fitted in the positioning groove 714 of the casing body 710.

The accommodating space 715 is adjacent to the rear surface 713, accommodates the conveying mechanism 73, opens upwardly at a top end of the casing body 710, and has two opposite ends. The lid body 711 is removably disposed on the casing body 710 so that the lid body 711 closes the accommodating space 715 and is operable to be opened. By virtue of the lid body 711 being operable to be opened, maintenance of the conveying mechanism 73 in the accommodating space 715 is relatively convenient. The first casing passage 716 is recessed in the rear surface 713, spatially communicates with one of the opposite ends of the accommodating space 715, and directs the inserting end 21 of the urinary catheter 2 to extend through the accommodating space 715. The second casing passage 717 spatially communicates with the positioning groove 714 and the other one of the opposite ends of the accommodating space 715, is aligned with the guiding hole 613 of the sleeve member 61, and directs the inserting end 21 of the urinary catheter 2 to extend through the guiding hole 613. In the first embodiment, a cross section of each of the first casing passage 716 and the second casing passage 717 corresponds in shape to the cross section of the urinary catheter 2 (i.e., the cross section of each of the first casing passage 716 and the second casing passage 717 is circular).

The casing 71 further includes a casing connector unit 720 that is removably connectable to the sleeve connector unit 615, and a plurality of mounting grooves 722. Specifically, the mounting grooves 722 are recessed in the inner dome-shaped surface 718, are spaced apart from each other, and spatially communicate with the positioning groove 714. In the first embodiment, the mounting grooves 722 are angularly spaced apart from each other, and the casing connector unit 720 includes a plurality of magnetic components 721 that are respectively bonded into the mounting grooves 722, that are flush with the inner dome-shaped surface 718, and that are respectively and magnetically attracted to the magnetic components 616 of the sleeve connector unit 615.

Figure 9:
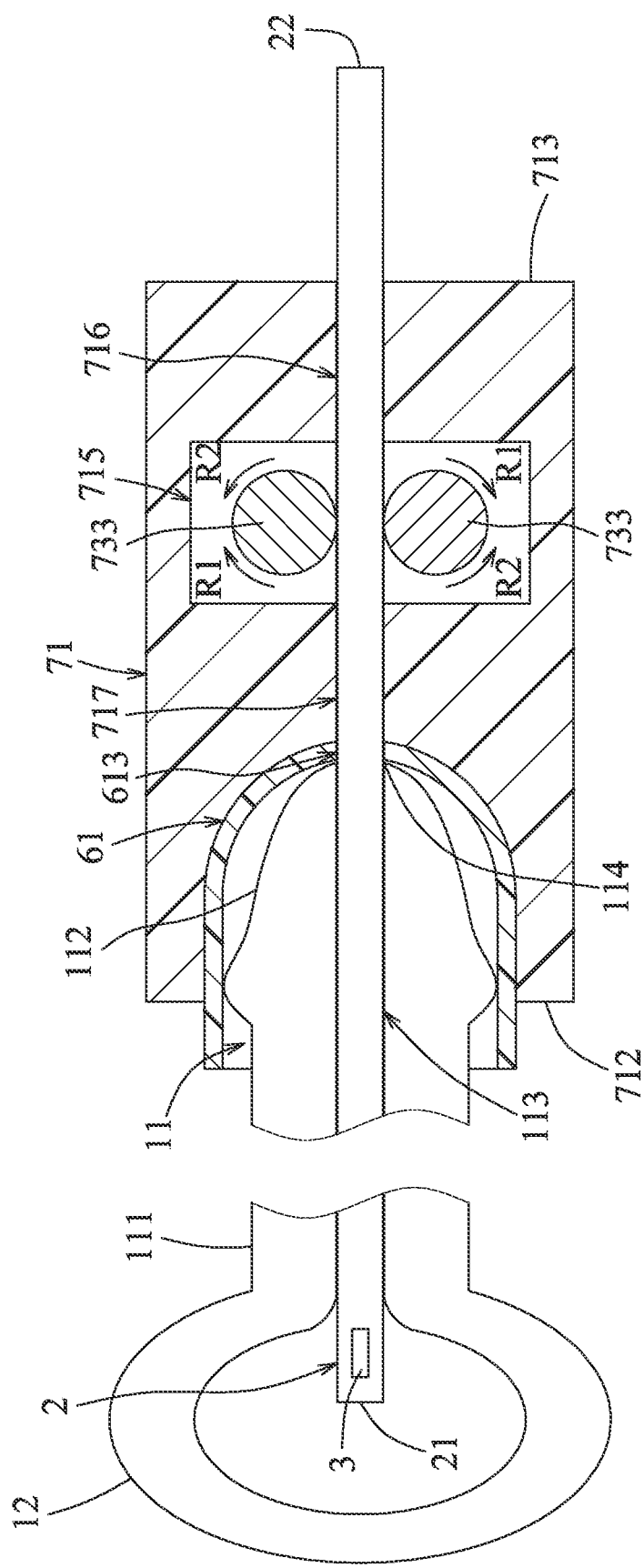
FIG. 9 is the same view as FIG. 8, but illustrating the urinary catheter being inserted into a bladder.

The conveying mechanism 73 is adapted for advancing the urinary catheter 2 to the guiding hole 613 of the sleeve member 61 such that the urinary catheter 2 is inserted into the external urethral orifice 114 of the glans 112 through the guiding hole 613. The conveying mechanism 73 includes a circuit board 731, two motors 732, two conveyor wheels 733, a processing unit 734, a wireless communication unit 735, a rechargeable battery 736 and an electrical connector 737. The motors 732 are mounted to the circuit board 731. The conveyor wheels 733 are respectively connected to top ends of the motors 732. The processing unit 734, the wireless communication unit 735, the rechargeable battery 736 and the electrical connector 737 are mounted to the circuit board 731. The conveyor wheels 733 are spaced apart from each other, and cooperatively clamp the urinary catheter 2 when the urinary catheter 2 extends through the first casing passage 716 into the accommodating space 715. Referring further to FIG. 9, each of the motors 732 is operable to drive the respective one of the conveyor wheels 733 to rotate in a first rotating direction (R1) or a second rotating direction (R2) opposite to the first rotating direction (R1). The conveyor wheels 733 can clamp the urinary catheter 2 and carry the same to move toward or away from the second casing passage 717.

The processing unit 734 is electrically coupled to the motors 732, the wireless communication unit 735 and the rechargeable battery 736, and controls the motors 732 to switch between an on state, in which the motors 732 urge the conveyor wheels 733 to rotate, and an off state, in which the conveyor wheels 733 cease to rotate. The wireless communication unit 735 transmit electrical signals via Bluetooth or Wi-Fi. The rechargeable battery 736 supplies electric power to the motors 732, the processing unit 734 and the wireless communication unit 735. A portion of the electrical connector 737 is exposed from the casing body 710, and is adapted to be connected to a power cable (not shown). Via the power cable, the electrical connector 737 transmits external electrical energy to the rechargeable battery 736 to charge the rechargeable battery 736.

The pressure sensor 3 is wirelessly and electrically coupled to the wireless communication unit 735 of the conveying mechanism 73. When the processing unit 734 of the conveying mechanism 73 receives one of the first and second pressure signals from the pressure sensor 3, the processing unit 734 switches the motors 732 into the off state so that the motors 732 cease to rotate or advance the conveying wheels 733.

The controller 8 is configured to be portable, and is wirelessly and electrically coupled to the wireless communication unit 735 of the conveying mechanism 73 so that the controller 8 is operable to wirelessly control the conveying assembly 7. Specifically, the controller 8 includes a power on button 81, a power off button 82, a forward movement button 83, a rearward movement button 84 and an emergency stop button 85. When the power on button 81 is pressed, the conveying assembly 7 is switched to a power-on state. When the power off button 82 is pressed, the conveying assembly 7 is switched to a power-off state. When the forward movement button 83 is pressed, the conveying assembly 7 is switched to a forward conveying state to advance the urinary catheter 2. When the rearward movement button 84 is pressed, the conveying assembly 7 is switched to a rearward conveying state to move the urinary catheter 2 rearward. When the emergency stop button 85 is pressed, the conveying assembly 7 is in a stop state to stop the urinary catheter 2 from moving. By pressing the different buttons of the controller 8, the conveying assembly 7 can be switched among the abovementioned operation states.

It is noted that, in certain embodiments, the controller 8 may be, but not limited to, a smart phone that is operable to control the conveying assembly 7 to switch among the abovementioned operation states via a mobile application therein.

Figure 4:
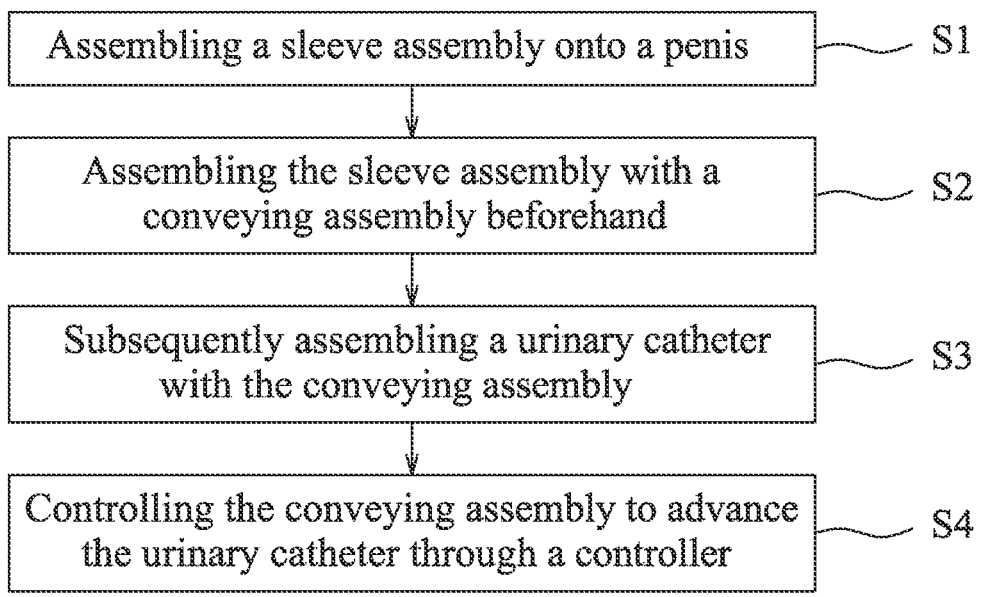
FIG. 4 is a flow diagram illustrating a first embodiment of a method of using the urinary catheterization system according to the disclosure.
Figure 5:
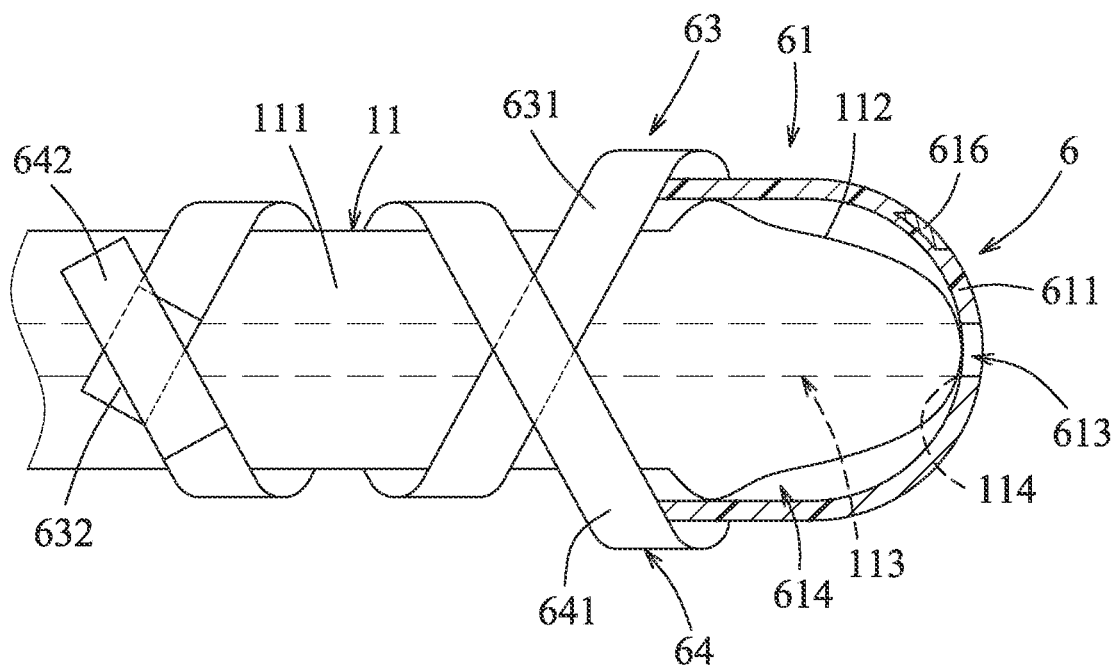
FIG. 5 is a fragmentary schematic view illustrating the sleeve assembly of the first embodiment being assembled onto the penis.

FIG. 4 illustrates a method of using the urinary catheterization system according to the disclosure, particularly, a first embodiment of the method which utilizes the first embodiment of the urinary catheterization system and which includes steps S1 to S4. Referring further to FIG. 5, in cooperation with FIG. 1, in step S1, the sleeve assembly 6 is assembled onto the penis 11. Specifically, in executing step S1, the glans 112 of the penis 11 is covered with the sleeve member 61 of the sleeve assembly 6 and is accommodated in the accommodating groove 614 of the sleeve member 61. By virtue of the sleeve assembly 6 being portable, it is convenient for a user to quickly cover the glans 112 with the sleeve member 61, and then to register the guiding hole 613 of the sleeve member 61 with the external urethral orifice 114 of the glans 112. By virtue of the sleeve member 61 including the dome-shaped cap portion 611 that matches the glans 112, the sleeve member 61 can be snugly fitted on the glans 112 to be prevented from moving relative to the glans 112. Afterwards, the sleeve member 61 is tied to the penis shaft 111. Specifically, the first band 63 is tightly wound around the penis shaft 111, and then the second band 64 is tightly wound around the penis shaft 111 and the first band 63. Then, one of the loop-surfaced components 642 of the second band 64 is stuck to the respective one of the hook-surfaced components 632 of the first band 63 so that the first band 63 and the second band 64 are firmly secured together. Consequently, the sleeve assembly 6 is firmly assembled onto the penis 11.

By virtue of the first and second bands 63, 64 winding around the penis shaft 111, and by virtue of the first and second bands 63, 64 being fastened to each other via the hook-surfaced components 632 and the loop-surfaced components 642 thereof, the sleeve assembly may suit penis shafts in different girth and length. Furthermore, by virtue of the loop-surfaced components 642 being respectively disposed on the opposite surfaces of the band body 641 of the second band 64, and by virtue of the hook-surfaced components 632 being respectively disposed on the opposite surfaces of the band body 631 of the first band 63, the first and second bands 63, 64 can stick to each other without needing to turn over the first and/or second bands 63, 64 from one side to the other side thereof, thereby saving time for the user.

It is noted that, in the first embodiment, the second band 64 may include only one loop-surfaced component 642, and the first band 63 may include only one hook-surfaced component 63.

Figure 6:
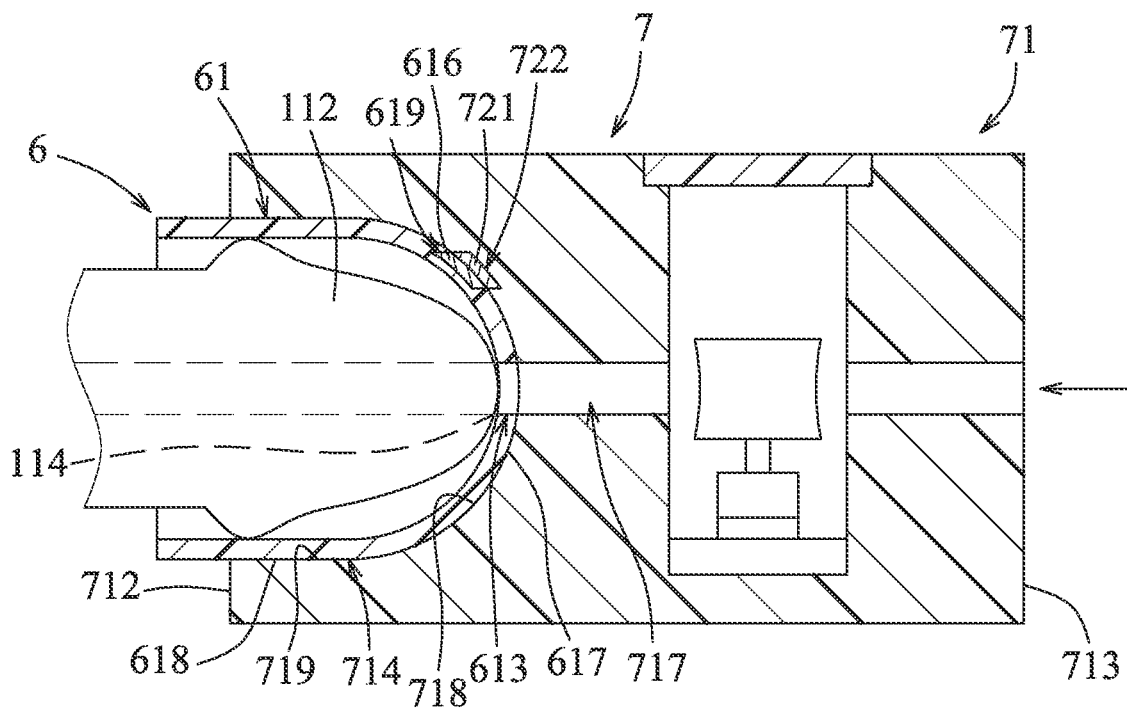
FIG. 6 is a sectional side view illustrating the conveying assembly of the first embodiment being mounted to the sleeve assembly.
Figure 7:
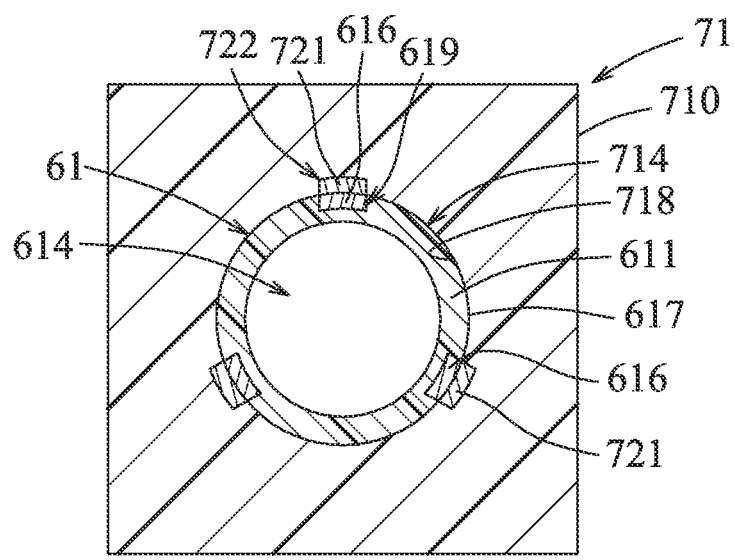
FIG. 7 is another sectional side view illustrating magnetic components of the conveying assembly being respectively and magnetically attracted to magnetic components of the sleeve assembly.

Referring further to FIGS. 6 and 7 in combination with FIG. 4, in steps S2 and S3, the sleeve assembly 6 is assembled with the conveying assembly 7 and the urinary catheter 2. Specifically, in executing step S2, the sleeve member 61 of the sleeve assembly 6 is sleeved into the positioning groove 714 of the casing 71 of the conveying assembly 7 beforehand. At this time, by virtue of the magnetic components 616 of the sleeve assembly 6 being flush with the outer dome-shaped surface 617, by virtue of the magnetic components 721 of the conveying assembly 7 being flush with the inner dome-shaped surface 718, and by virtue of the inner dome-shaped surface 718 and the inner surrounding surface 719 respectively abutting against the outer dome-shaped surface 617 and the outer surrounding surface 618, the casing 71 is prevented from shaking or moving relative to the sleeve member 61 so that the second casing passage 717 is precisely aligned with the guiding hole 613.

In addition, if the magnetic components 721 of the casing 71 are not respectively registered with the magnetic components 616 of the sleeve member 61, a user may rotate the casing 71 relative to the sleeve member 61 to register the magnetic components 721 of the casing 71 with the magnetic components 616 of the sleeve member 61 so that the magnetic components 721 are respectively and magnetically attracted to the magnetic components 616. By virtue of the magnetic components 721 being respectively and magnetically attracted to the magnetic components 616, the sleeve member 61 is firmly sleeved into the casing 71 and the casing 71 is prevented from moving relative to the sleeve member 61.

Figure 8:
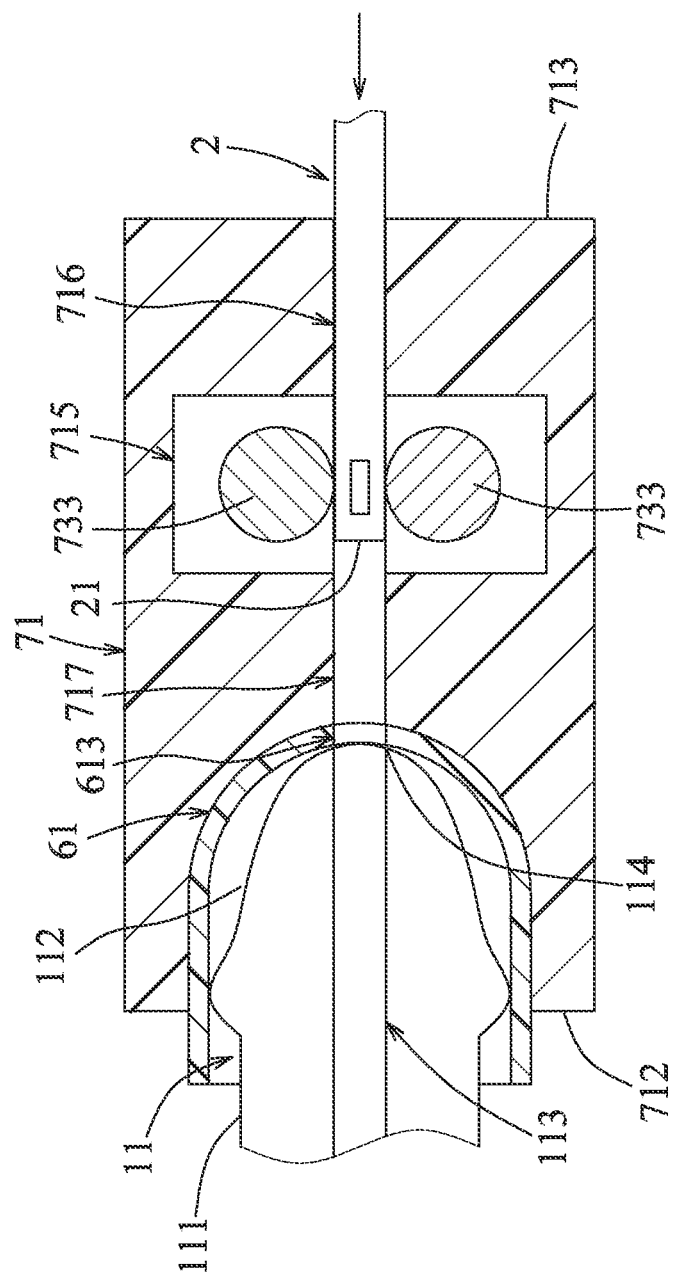
FIG. 8 is a sectional top view illustrating a urinary catheter of the first embodiment being assembled to the conveying assembly.

Referring further to FIG. 8, in executing step S3 which is subsequent to step 2, the urinary catheter 2 is subsequently inserted into the casing 71 such that the conveying mechanism 73 that is disposed in the casing 71 clamps the urinary catheter 2. Specifically, the inserting end 21 of the urinary catheter 2 is inserted into the first casing passage 716 through the rear surface 716 of the casing 71, and then is inserted into the accommodating space 715 through the first casing passage 716 so that the urinary catheter 2 is inserted between the conveyor wheels 733. At this time, the urinary catheter 2 is clamped by the conveyor wheels 733.

Referring further to FIG. 9, in step S4, the conveying assembly 7 is controlled by the controller 8 to advance the urinary catheter 2 to the guiding hole 613 of the sleeve member 61 of the sleeve assembly 6 so that the urinary catheter 2 is inserted into the external urethral orifice 114 of the glans 112 of the penis 11 through the guiding hole 613. Specifically, the power on button 81 is pressed to turn on the conveying assembly 7, and then the forward movement button 83 is pressed to switch the conveying assembly 7 to the forward conveying state. At this time, the processing unit 734 controls the motors 732 to drive the conveyor wheels 733 to respectively rotate in the first rotating direction (R1) and the second rotating direction (R2) (in FIG. 9, the upper one of the conveyor wheels 733 rotates in the first rotating direction (R1) and the lower one of the conveyor wheels 733 rotates in the second rotating direction (R2)) so that the urinary catheter 2 is moved forward. Consequently, the inserting end 21 of the urinary catheter 2 is sequentially moved through the accommodating space 715, the second casing passage 717, the guiding hole 613, the external urethral orifice 114, and is then inserted into the urethra 113.

By virtue of the cross section of each of the guiding hole 613, the first casing passage 716 and the second casing passage 717 corresponding in shape to the cross section of the urinary catheter 2, when the urinary catheter 2 is advanced, the urinary catheter 2 is prevented from shaking, and is smoothly and precisely inserted into the urethra 113 through the external urethral orifice 114.

If a patient has the problem of urethral stricture or benign prostatic hyperplasia, the pressure sensor 3 that is adjacent to the inserting end 21 of the urinary catheter 2 may detect a pressure whose value is larger than the preset value when the inserting end 21 of the urinary catheter 2 is in the urethra 113, and thus the pressure sensor 3 generates the first pressure signal. When the processing unit 734 receives the first pressure signal from the pressure sensor 3 via the wireless communication unit 735, the processing unit 734 switches the motors 732 to the off state so the motors 732 cease to urge the conveying wheels 733 to advance the urinary catheter 2. Therefore, misuse of an incorrect urinary catheter that does not fit the urethra 113 of the patient is avoided, and the patient is prevented from getting hurt by the urinary catheter 2. If the patient does not feel uncomfortable, the forward movement button 83 may be pressed again so that the conveyor wheels 733 continue to urge the urinary catheter 2 to move forward in the urethra 113.

If a patient does not has the urethral stricture or benign prostatic hyperplasia problems, the pressure sensor 3 may not detect a pressure whose value is larger than the preset value, and thus the urinary catheterization system will not suddenly cease to urge the urinary catheter 2 to move in the urethra 113.

When the pressure sensor 3 switches from the first detected state (described hereinbefore) to the second detected state where no pressure is detected (described hereinbefore), it indicates that the inserting end 21 of the urinary catheter 2 has been inserted into a bladder 12. Consequently, the pressure sensor 3 generates the second pressure signal. When the processing unit 734 receives the second pressure signal from the pressure sensor 3 via the wireless communication unit 735, the processing unit 734 switches the motors 732 to the off state so the motors 732 cease to urge the conveying wheels 733 to advance the urinary catheter 2. The operation for insertion of the urinary catheter 2 into the bladder 12 through the penis 11 is therefore completed. At this time, the urinary catheter 2 is able to drain urine from the bladder 12, and the urine will flow from the inserting end 21 through the rear end 22 of the urinary catheter 2 into the urine collector.

A user can remove the urinary catheter 2 from the bladder 12 and the penis 11 by pressing the rearward movement button 84. When the rearward movement button 84 is pressed, the conveying assembly 7 is switched to the rearward conveying state, and the processing unit 734 controls the motors 732 to urge the conveyor wheels 733 to respectively rotate in the second rotating direction (R2) and the first rotating direction (R1) (in FIG. 9, the upper one of the conveyor wheels 733 rotates in the second rotating direction (R2) and the lower one of the conveyor wheels 733 rotates in the first rotating direction (R1)) so that the urinary catheter 2 is moved rearward. Consequently, the inserting end 21 of the urinary catheter 2 is sequentially removed from the bladder 12, the urethra 113, the external urethral orifice 114, the guiding hole 613 and the second casing passage 717. The urinary catheter 2 keeps moving rearwardly until the rotation of the conveyor wheels 733 does not cause the urinary catheter 2 to move. At this time, the user can draw the urinary catheter 2 out from the accommodating space 715 and the first casing passage 716 sequentially so that the urinary catheter 2 is removed from the conveying assembly 7.

Figure 10:
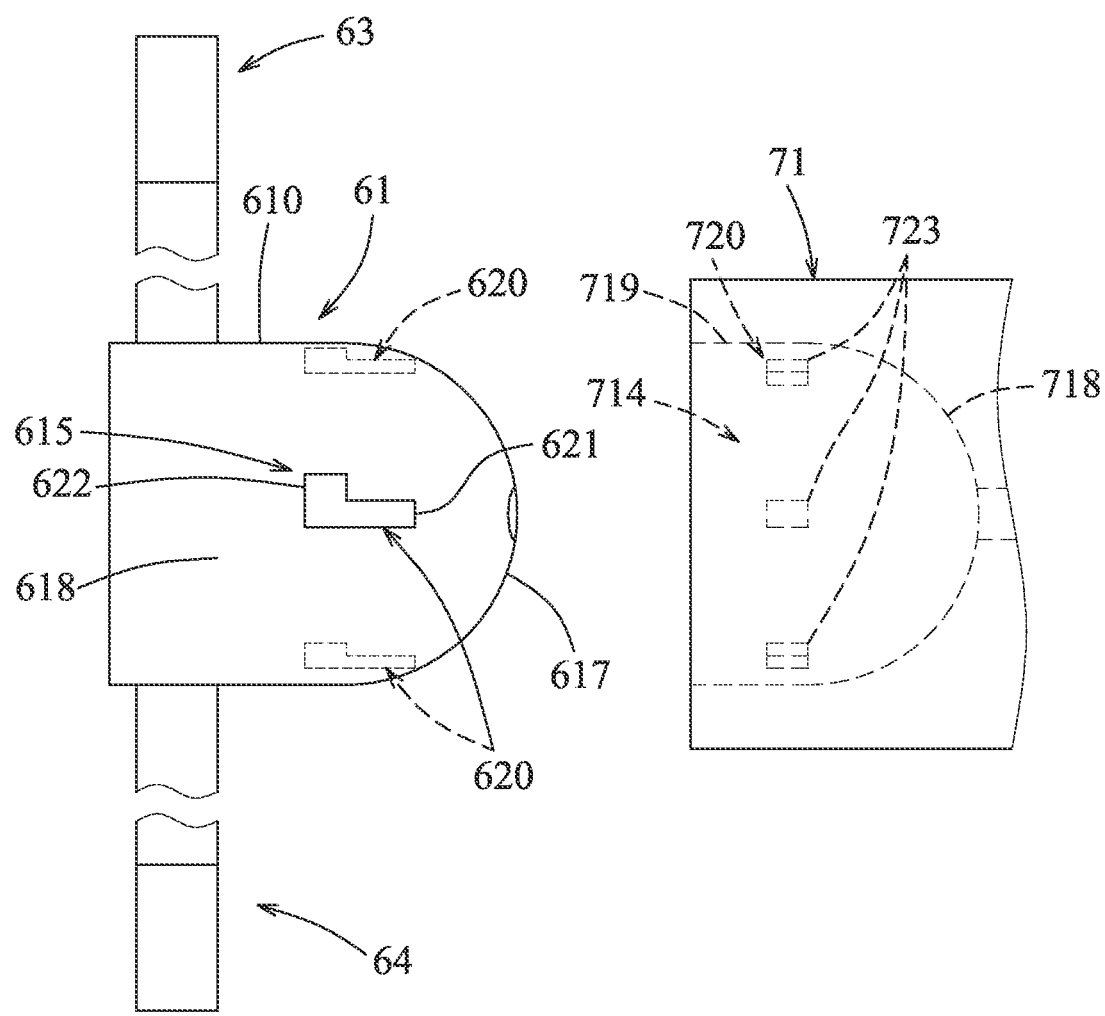
FIG. 10 is a fragmentary top view illustrating a sleeve assembly and a portion of a conveying assembly of a second embodiment of the urinary catheterization system according to the disclosure.
Figure 11:
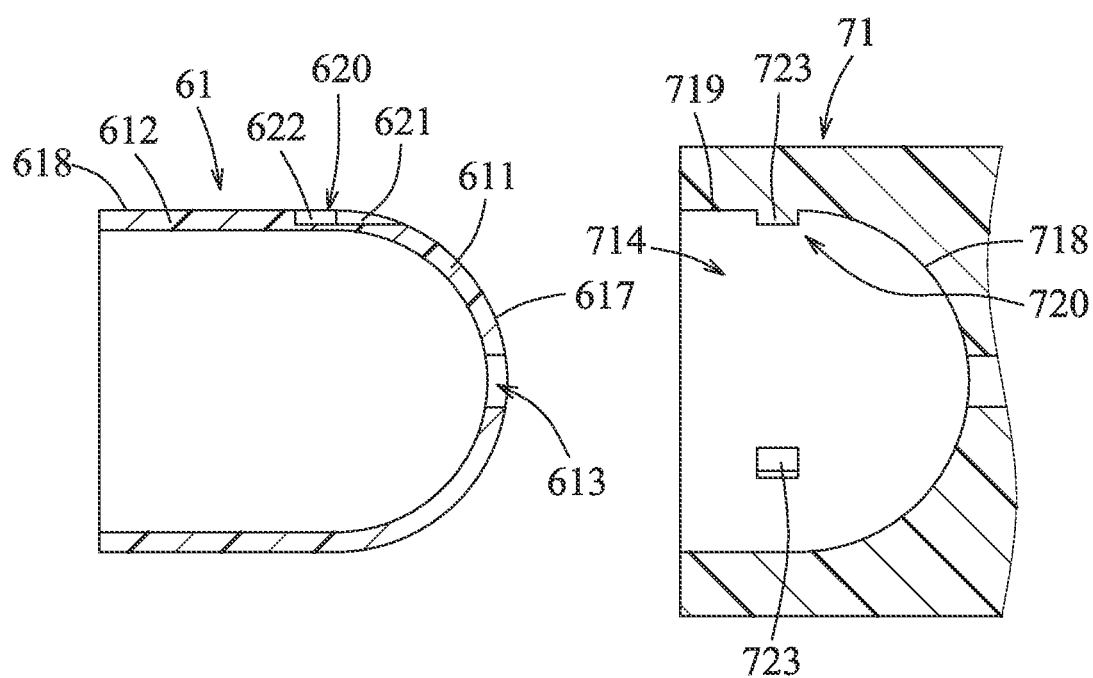
FIG. 11 is a fragmentary sectional view illustrating the sleeve assembly and a portion of the conveying assembly of the second embodiment.

Referring to FIGS. 10 and 11, a second embodiment of the urinary catheterization system according to the disclosure is generally similar to the first embodiment, but includes differences lying in the sleeve connector unit 615 of the sleeve assembly 6 and the casing connector unit 720 of the conveying assembly 7.

In the second embodiment, the sleeve connector unit 615 has a plurality of engaging grooves 620 that are formed at the sleeve main body 610 and that are spaced apart from each other. Specifically, the engaging grooves 620 are angularly spaced apart from each other. Each of the engaging grooves 620 is configured to be L-shaped, and has a guiding portion 621 that is elongated, and an engaging portion 622 that is perpendicularly connected to one end of the guiding portion 621. The guiding portion 621 is recessed in the outer dome-shaped surface 617 and the outer surrounding surface 618. The engaging portion 622 is recessed in the outer surrounding surface 618. The casing connector unit 720 includes a plurality of engaging protrusions 723 that are formed on the inner surrounding surface 719 of the casing body 710 at intervals to protrude into the positioning groove 714, that are adjacent to the inner dome-shaped surface 718 of the casing body 710, and that respectively engage the engaging grooves 620.

Figure 12:
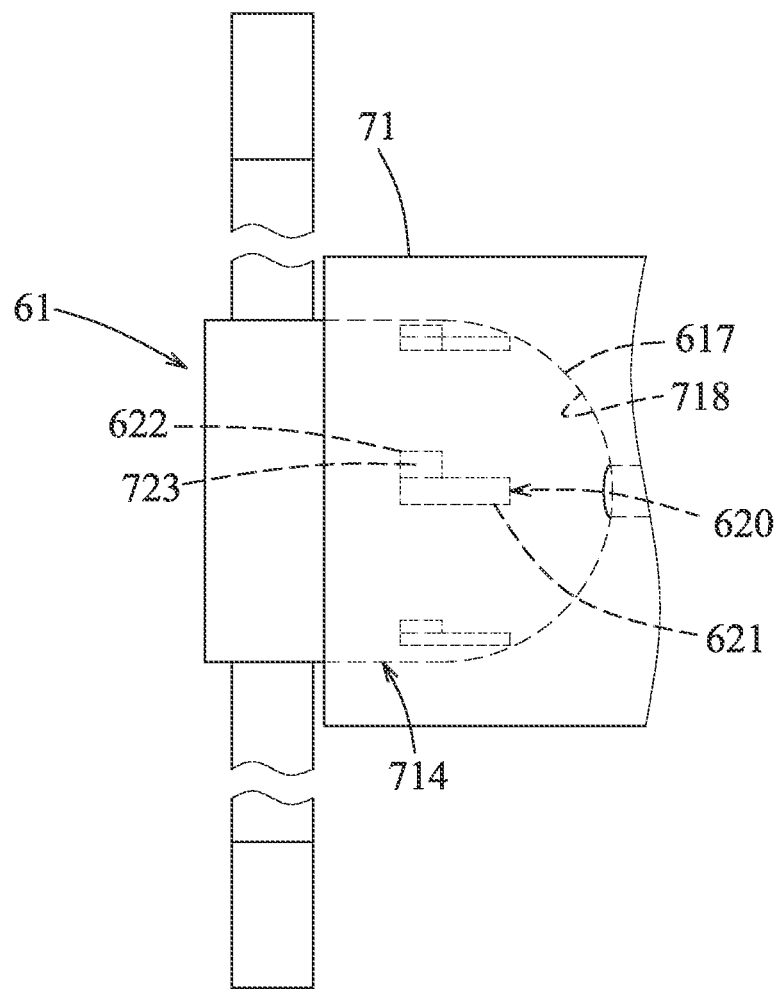
FIG. 12 is the same view as FIG. 10, but illustrating the sleeve assembly and a portion the conveying assembly of the second embodiment in an assembled state.

Referring further to FIG. 12, in executing step S2, the engaging protrusions 723 have to be respectively aligned with guiding portions 621 of the engaging grooves 620 before the sleeve member 61 is sleeved into the positioning groove 714. Therefore, when the sleeve member 61 is sleeved into the positioning groove 714, the engaging protrusions 723 respectively extend into the guiding portions 621. Afterwards, when the outer dome-shaped surface 617 abuts against the inner dome-shaped surface 718, the engaging portions 621 are respectively located at the ends of the guiding portions 621 and are respectively aligned with the engaging portions 622. At this time, when the casing 71 is rotated relative to the sleeve member 61, the engaging protrusions 723 respectively extend into and engage the engaging portions 622 of the engaging grooves 620. Consequently, the casing 71 and the sleeve member 61 are firmly assembled.

Figure 13:
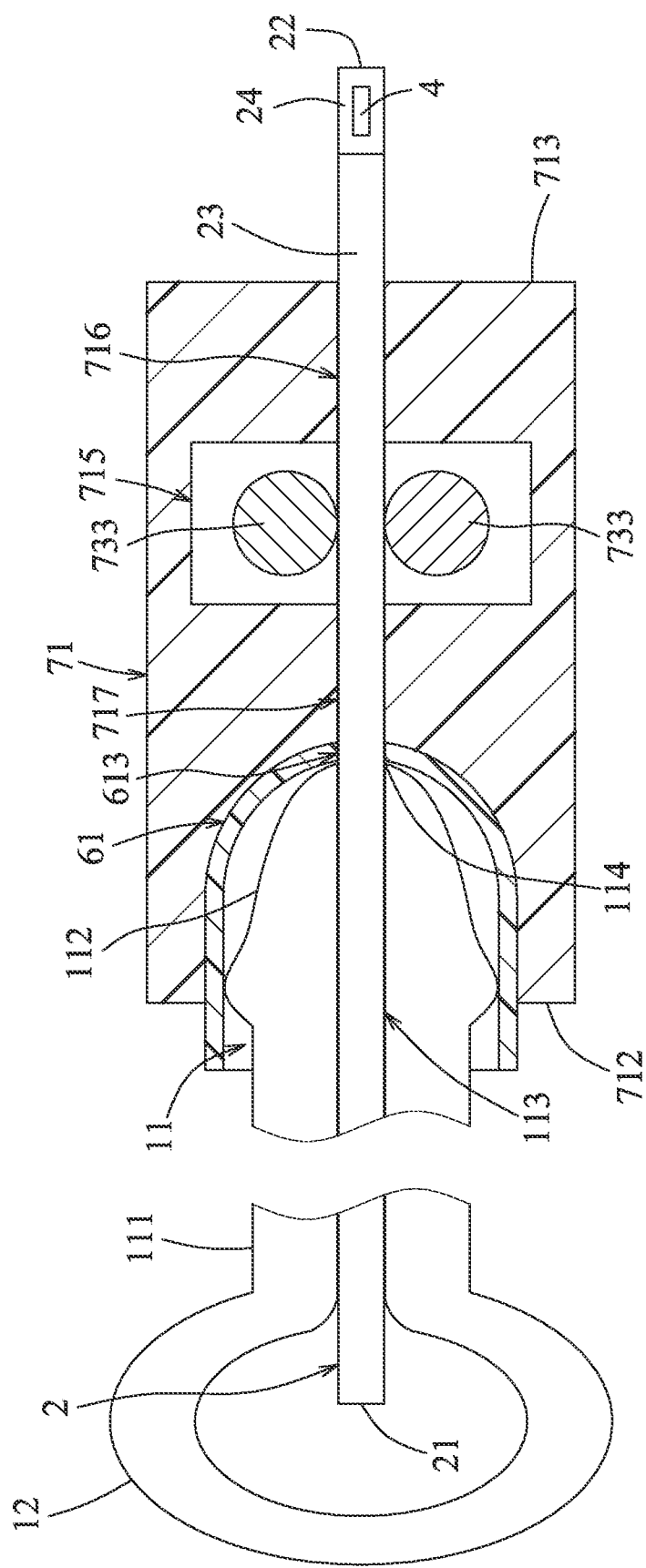
FIG. 13 is a fragmentary schematic view illustrating a urinary catheter of a third embodiment of the urinary catheterization system according to the disclosure being inserted into the bladder.

Referring to FIG. 13, in cooperation with FIG. 3, a third embodiment of the urinary catheterization system according to the disclosure is generally similar to the first embodiment, but includes a different configuration of the urinary catheter 2.

In the third embodiment, the urinary catheter 2 further has a transparent section 24 that is adjacent to the rear end 22. The urinary catheterization system further includes a photodetector 4 that is mounted to the transparent section 24, that generates a light signal when detecting passage of the urine through the transparent section 24, and that is electrically coupled (e.g., wirelessly) to the wireless communication unit 735 of the conveying mechanism 73.

When the inserting end 21 of the urinary catheter 2 is inserted into the bladder 12 and when the urine in the bladder 12 flows out of the urinary catheter 2, the photodetector 4 detects passage of the urine through the transparent section 24 and generates the light signal. When the processing unit 734 receives the light signal from the photodetector 4 via the wireless communication unit 735, the processing unit 734 switches the motors 732 to the off state so that the motors 732 cease to urge the conveying wheels 733 to advance the urinary catheter 2. So far, for the third embodiment, the insertion of the urinary catheter 2 into the bladder 12 through the penis 11 has been completed.

Figure 14:
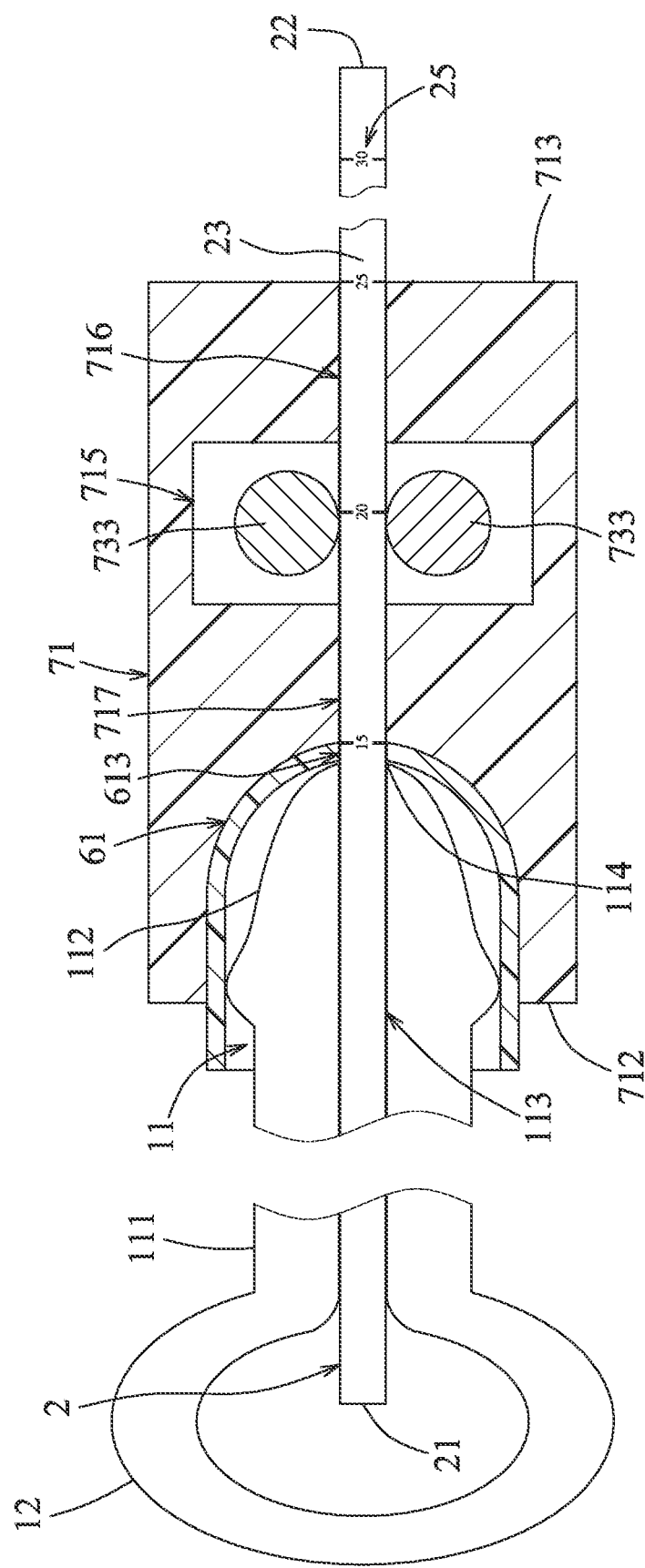
FIG. 14 is a fragmentary schematic view illustrating a urinary catheter of a fourth embodiment of the urinary catheterization system according to the disclosure being inserted into the bladder.

Referring to FIG. 14, a fourth embodiment of the urinary catheterization system according to the disclosure is generally similar to the first embodiment, but includes a different configuration of the urinary catheter 2.

In the fourth embodiment, the urinary catheter 2 further has a length measurement scale 25 that is engraved on the outer catheter surface 23 along an axial direction of the urinary catheter 2, and that has a plurality of numerical values for length measurement. In this embodiment, the length measurement scale 25 is configured to have a maximum length value, for example, 30 centimeters. Since the distance between the external urethral orifice 114 and the bladder 12 of an ordinary man is arranged to be about 20 centimeters, and the distance between the rear surface 713 of the casing 71 and the guiding hole 613 of the sleeve member 61 is arranged to be 5 centimeters, when the rear surface 713 of the casing 71 is aligned with one of the numerical values between 25 cm and 30 cm of the length measurement scale 25, it means that the inserting end 21 of the urinary catheter 2 has been inserted into the bladder 12. At this time, a user may press the emergency stop button 85 so that the motors 732 cease to urge the conveying wheels 733 to advance the urinary catheter 2.

Figure 15:
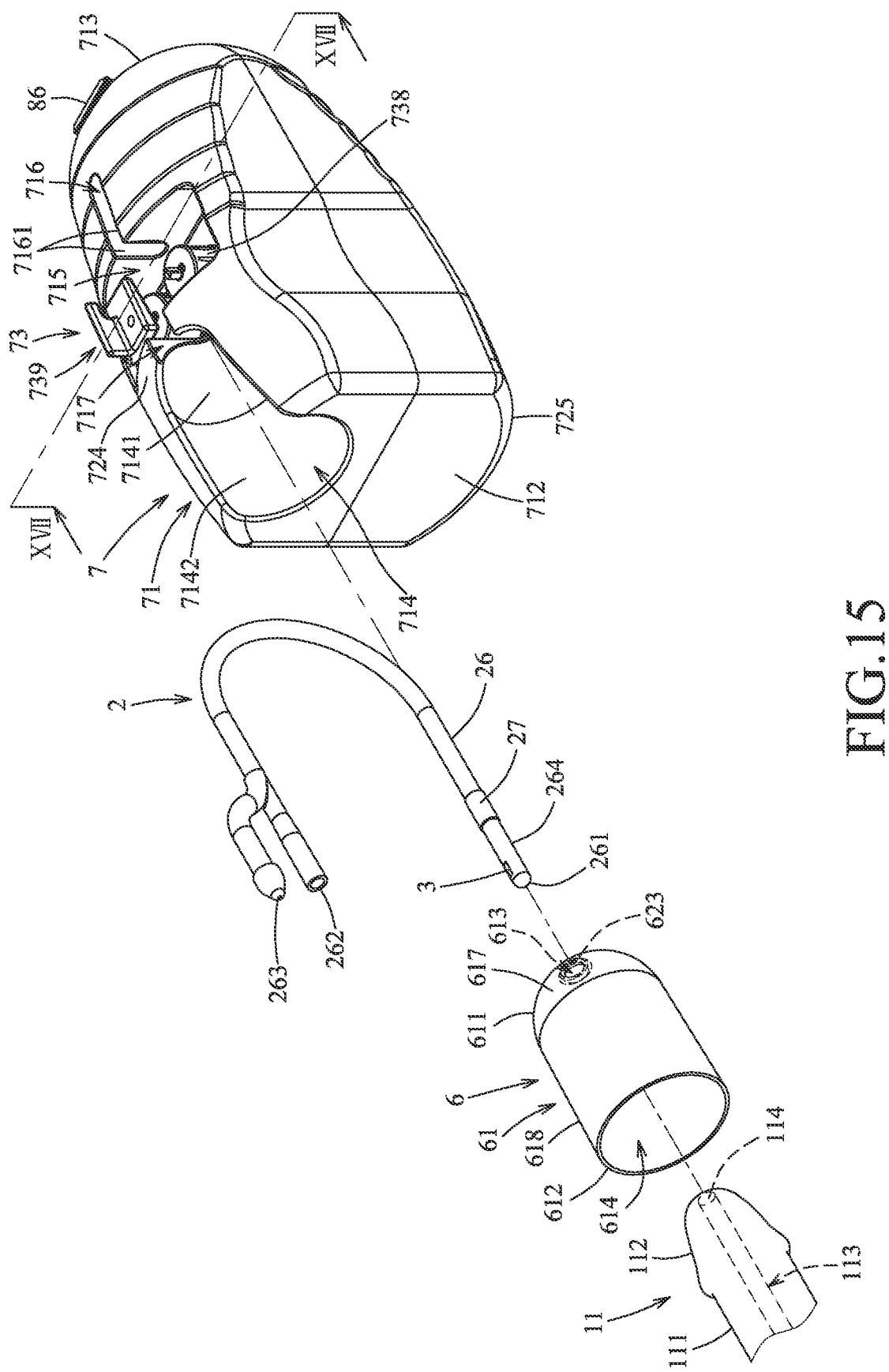
FIG. 15 is a partly exploded perspective view of a fifth embodiment of the urinary catheterization system according to the disclosure, and a fragmentary view of the penis.
Figure 16:
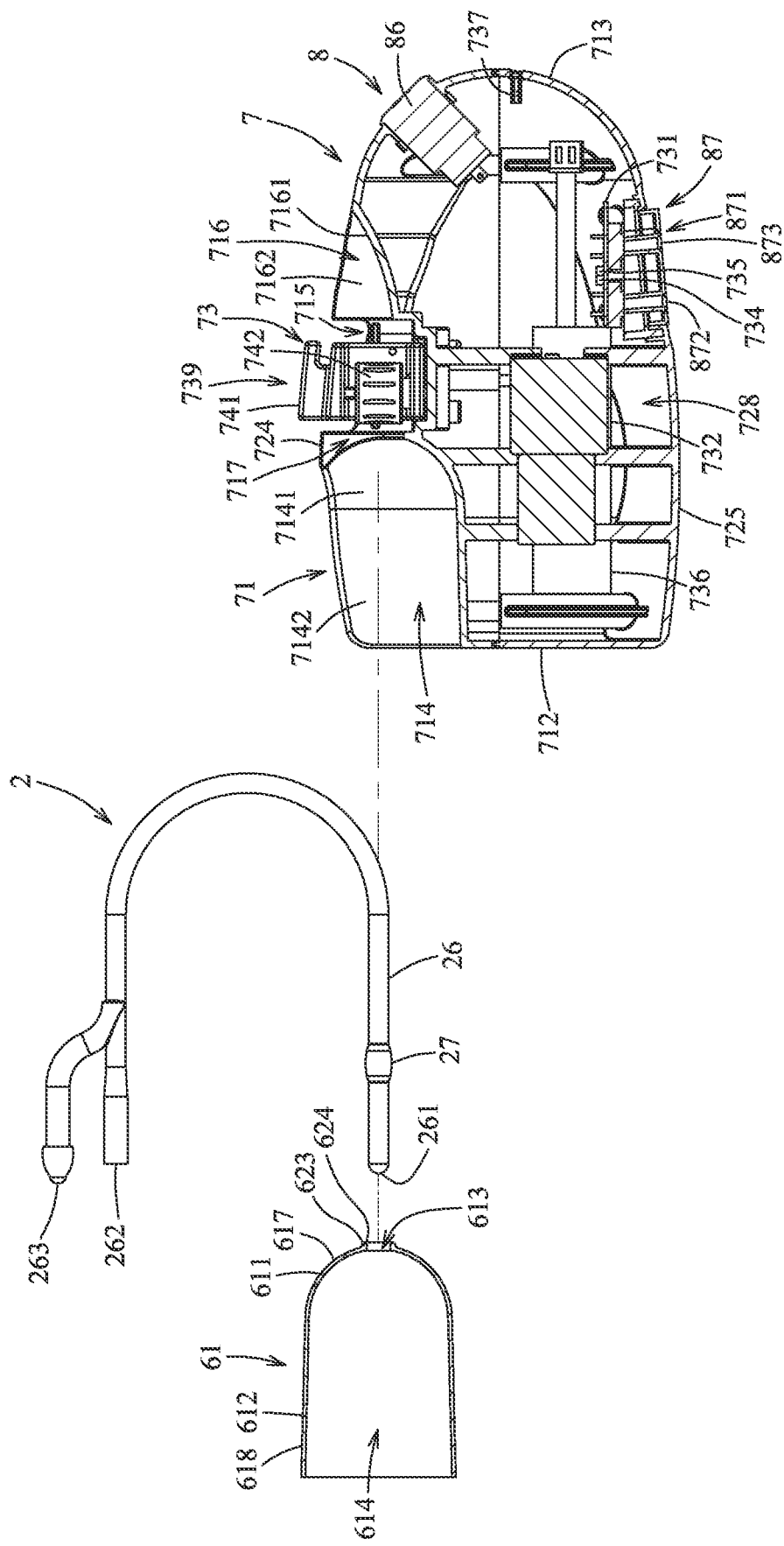
FIG. 16 is a partly sectional view of the fifth embodiment.

Referring to FIGS. 15 and 16, a fifth embodiment of the urinary catheterization system according to the disclosure is generally similar to the first embodiment, but includes the differences lying in structures of the urinary catheter 2 and the urinary catheter conveying device 5.

In the fifth embodiment, the urinary catheter 2 is configured to be an indwelling urinary catheter, and includes a tube body 26 and a balloon body 27. The tube body 26 has an inserting end 261, a rear end 262, a syringe connection end 263 and an outer catheter surface 264. The inserting end 261 is adapted to be inserted into the external urethral orifice 114 of the glans 112. The rear end 262 is adapted to be connected to a urine collector (not shown). The syringe connection end 263 is adapted to be connected to a syringe (not shown). The balloon body 27 is disposed on the tube body 26, is adjacent to the inserting end 261, and is adapted to be inserted into the bladder 12. The size of the balloon body 27 increases when the balloon body 27 is filled with fluid, such as water or gas, that is injected into the syringe connection end 263 by the syringe and that flows through the tube body 26 into the balloon body 27.

The sleeve member 61 is made from a resilient material, such as polysiloxane. By virtue of the sleeve member 61 being resilient, the sleeve member 61 can be sleeved onto the glans 112 of the penis 11 in a tight fit so that the first and second bands 63, 64 may be dispensed with. This reduces the manufacturing cost and facilitates assembly of the sleeve assembly 6 onto the penis 11. It is noted that, according to operational requirements, in other modifications of the fifth embodiment, the sleeve member 61 may be connected to the first and second bands 63, 64 as in the first embodiment.

The sleeve member 61 further includes a protruding ring 623 that extends centrally through and protrudes from the dome-shaped portion 611 opposite to the tubular portion 612, that defines the guiding hole 613, and that has a chamfered surface 624 surrounding the guiding hole 613. The chamfered surface 624 directs or guides the inserting end 261 of the urinary catheter 2 to extend into the guiding hole 613 when contacting the inserting end 261 of the urinary catheter 2.

The casing 71 further has a top surface 724 that interconnects the front surface 712 and the rear surface 713, a bottom surface 725 that interconnects the front surface 712 and the rear surface 713 and that is located under the top surface 724, and an inner space 728. The positioning groove 714 is recessed in the front surface 712 and the top surface 724. The top surface 724 is recessed to form the accommodating space 715 that accommodates a portion of the conveying mechanism 73, the first casing passage 716 that spatially communicates with a rear side of the accommodating space 715 opposite to the positioning groove 714, and the second casing passage 717 that is located between the positioning groove 714 and the accommodating space 715, and that is opposite to the first casing passage 716. The tube body 26 of the urinary catheter 2 extends through the positioning groove 714, the second casing passage 717, the accommodating space 715 and the first casing passage 716. The inner space 728 spatially communicates with a bottom side of the accommodating space 715, and accommodates another portion of the conveying mechanism 73.

Figure 17:
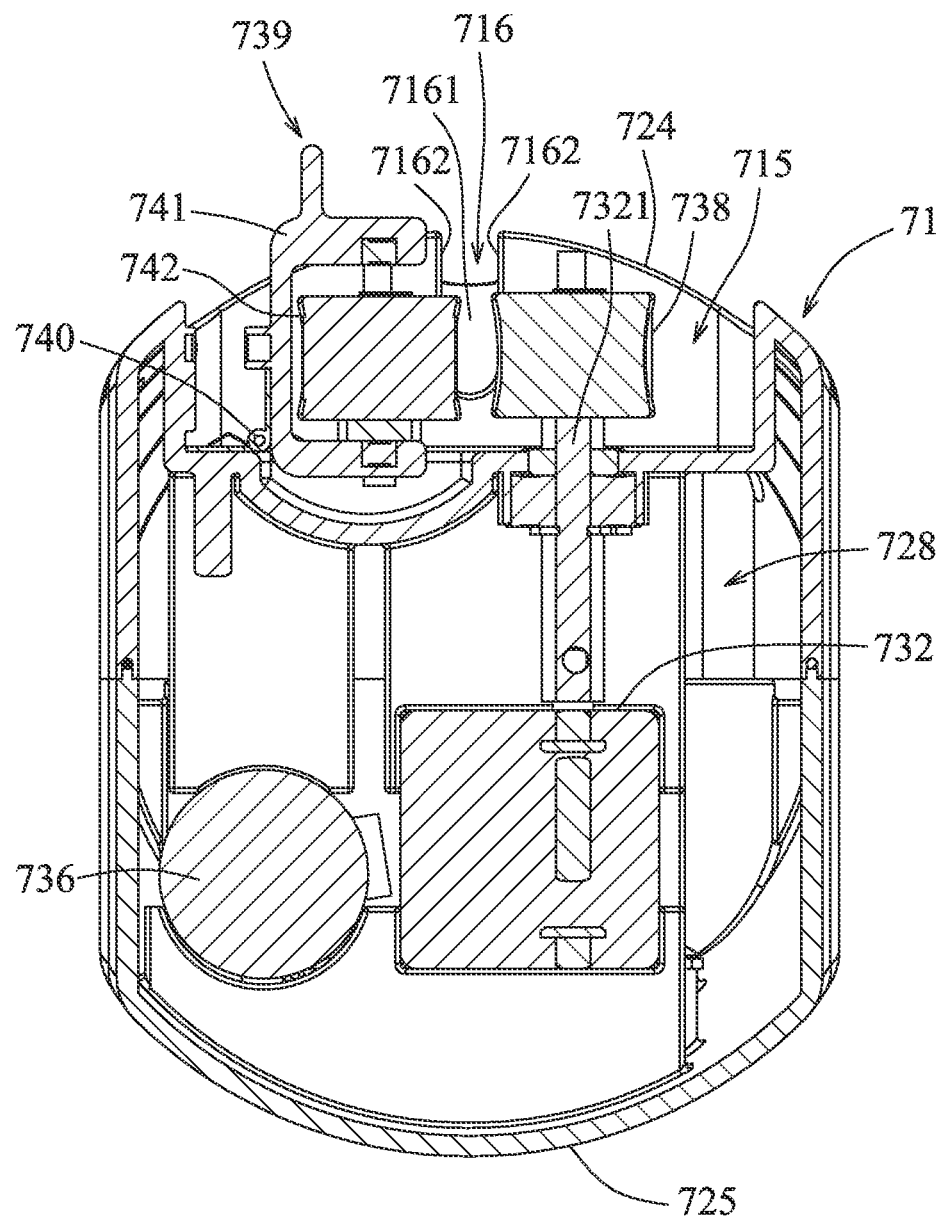
FIG. 17 is a sectional view taken along line XVII-XVII in FIG. 15, illustrating a frame of the fifth embodiment being in a first position.

Referring further to FIG. 17, the casing 71 further has a first curved positioning surface 7141, and a second curved positioning surface 7142 that is connected to a front end of the first curved positioning surface 7141 and that cooperates with the first curved positioning surface 7141 to define the positioning groove 714. The first curved positioning surface 7141 and the second curved positioning surface 7142 respectively correspond in shape to part of the outer dome-shaped surface 617 and part of the outer surrounding surface 618 so that when the casing 71 is mounted to the sleeve member 61, the first curved positioning surface 7141 abuts against the outer dome-shaped surface 617 and restrains movement of the dome-shaped cap portion 611 of the sleeve member 61, and the second curved positioning surface 7142 abuts against the outer surrounding surface 618 and restrains movement of the tubular portion 612 of the sleeve member 61. Thus, the casing 71 is suitably mounted to the sleeve member 61.

The casing 71 further has a curved supporting surface 7161 and two restraining surfaces 7162. The curved supporting surface 7161 extends from the top surface 724 of the casing 71 to the accommodating space 715 and supports the urinary catheter 2. The restraining surfaces 7162 are respectively connected to two sides of the curved supporting surface 7161 which are opposite to one another in a direction transverse to an extending direction of the curved supporting surface 7161. The restraining surfaces 7162 cooperate with the curved supporting surface 7161 to define the first casing passage 716, and are adapted for restraining movement of the urinary catheter 2 in a direction transverse to the urinary catheter 2.

Figure 18:
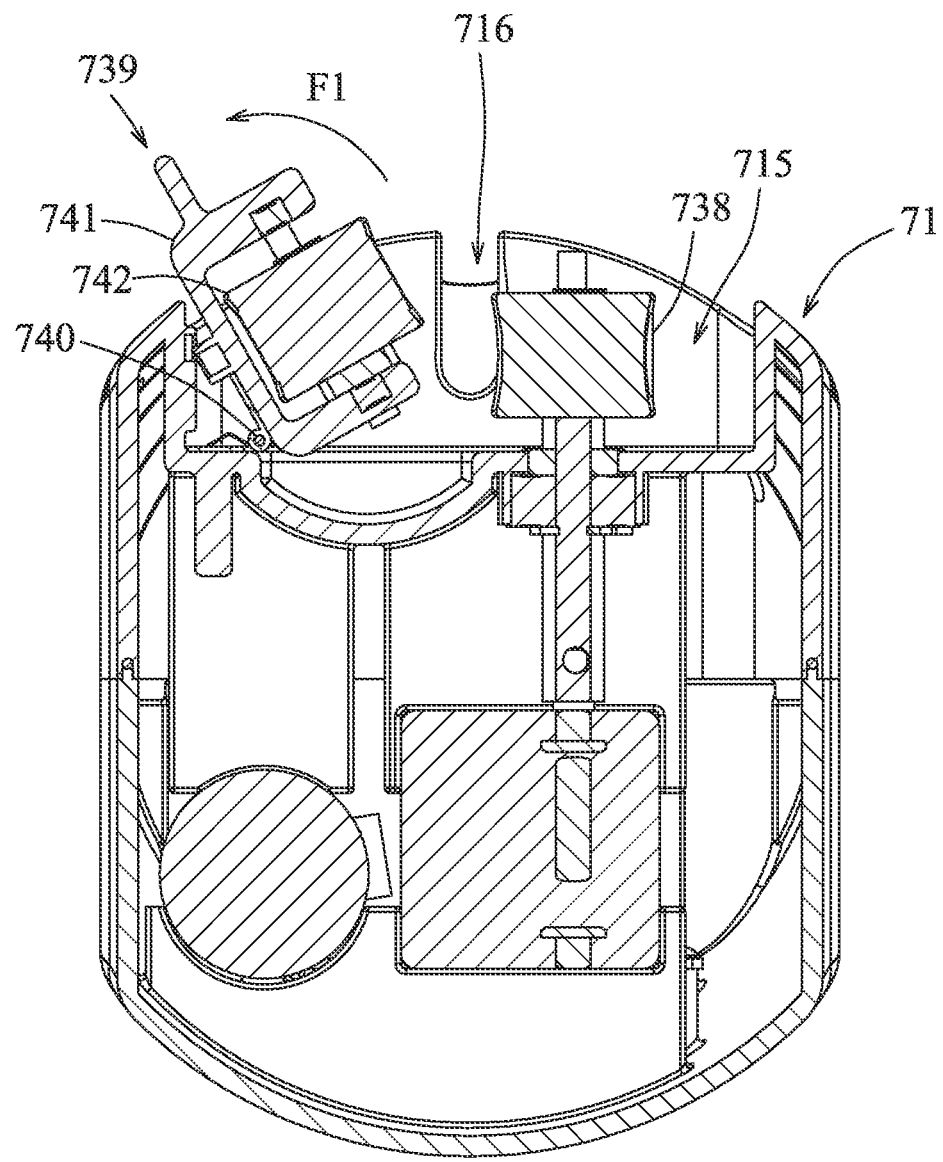
FIG. 18 is a view similar to FIG. 17, but illustrating the frame of the fifth embodiment being in a second position.

Referring further to FIG. 18, the circuit board 731, the rechargeable battery 736 and the electrical connector 737 are disposed in the inner space 728. The electrical connector 737 is exposed from the rear surface 713 (see FIG. 16). In the fifth embodiment, the conveying mechanism 73 includes one motor 732 that is disposed on the casing 71. Specifically, the motor 732 is configured to be a worm drive motor, is mounted in the inner space 728, and includes a drive shaft 7321 that extends from the inner space 728 into the accommodating space 715. The conveying mechanism 73 further includes a driving conveyor wheel 738 and a pressing unit 739. The driving conveyor wheel 738 is located in the accommodating space 715 and is connected to the motor 732. Specifically, the driving conveyor wheel 738 is sleeved around a top end of the drive shaft 7321 of the motor 732, and can be driven by the drive shaft 7321 to rotate. The pressing unit 739 is located in the accommodating space 715, is movably connected to the casing 71, is spaced apart from the driving conveyor wheel 738, and is operable to move towards or away from the driving conveyor wheel 738 so as to clamp the urinary catheter 2 against the driving conveyor wheel 738 or unclamp the urinary catheter 2.

Specifically, the pressing unit 739 includes a hinge 740, a frame 741 and a driven conveyor wheel 742. The hinge 740 is connected to the casing 71. The frame 741 is mounted to the hinge 740 and is rotatable relative to the casing 71 via the hinge 740. The driven conveyor wheel 742 is rotatably mounted to the frame 741 and is co-movable with the frame 741 relative to the casing 71. The frame 741 is operable to rotate relative to the casing 71 between a first position (see FIG. 17) and a second position (see FIG. 18). When the frame 741 is in the first position, the driven conveyor wheel 742 is proximate to the driving conveyor wheel 738 and cooperates with the driving conveyor wheel 738 to clamp the urinary catheter 2. When the frame 741 is in the second position, the driven conveyor wheel 742 is in an inclining position, is distal from the driving conveyor wheel 738 and unclamps the urinary catheter 2.

Referring to FIG. 16 again, the controller 8 includes a switch 86 and a controlling unit 87 that are disposed at the inner space 728. The switch 86 is electrically coupled to the circuit board 731 via wires (not shown), is exposed from the rear surface 713, and is pressable to switch the conveying assembly 7 between the power-on state and the power-off state. The controlling unit 87 is electrically coupled to a bottom side of the circuit board 731 and includes an operation button 871. The operation button 871 has a forward movement press portion 872 and a rearward movement press portion 873 that is located at a rear of the forward movement press portion 872. When the forward movement press portion 872 is pressed, the conveying assembly 7 is switched to the forward conveying state. When the rearward movement press portion 873 is pressed, the conveying assembly 7 is switched to the rearward conveying state.

Figure 19:
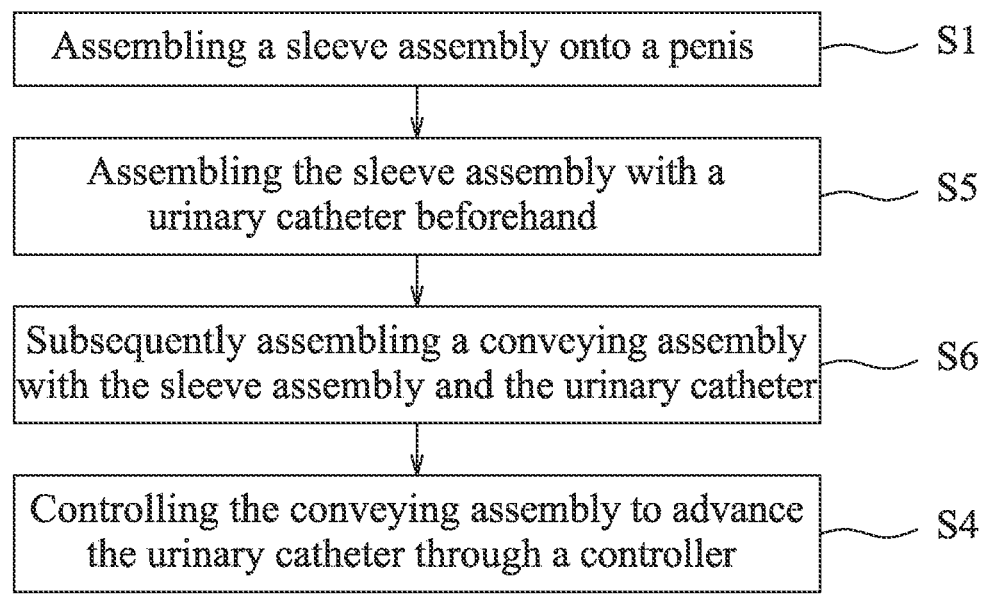
FIG. 19 is a flow diagram illustrating a second embodiment of the method of using the urinary catheterization system according to the disclosure, in which the fifth embodiment is used.

FIG. 19 illustrates a second embodiment of the method of using the urinary catheterization system according to the disclosure which is generally similar to the first embodiment illustrated in FIG. 4. However, the second embodiment of the method utilizes the fifth embodiment of the urinary catheterization system, and has differences lying in steps S5 and S6. In step S5, the inserting end 261 of the urinary catheter 2 is inserted into the guiding hole 613 of the sleeve member 61 beforehand. In step S6, the casing 71 of the conveying assembly 7 is subsequently mounted to the sleeve member 61 of the sleeve assembly 6 and the urinary catheter 2.

Figure 20:
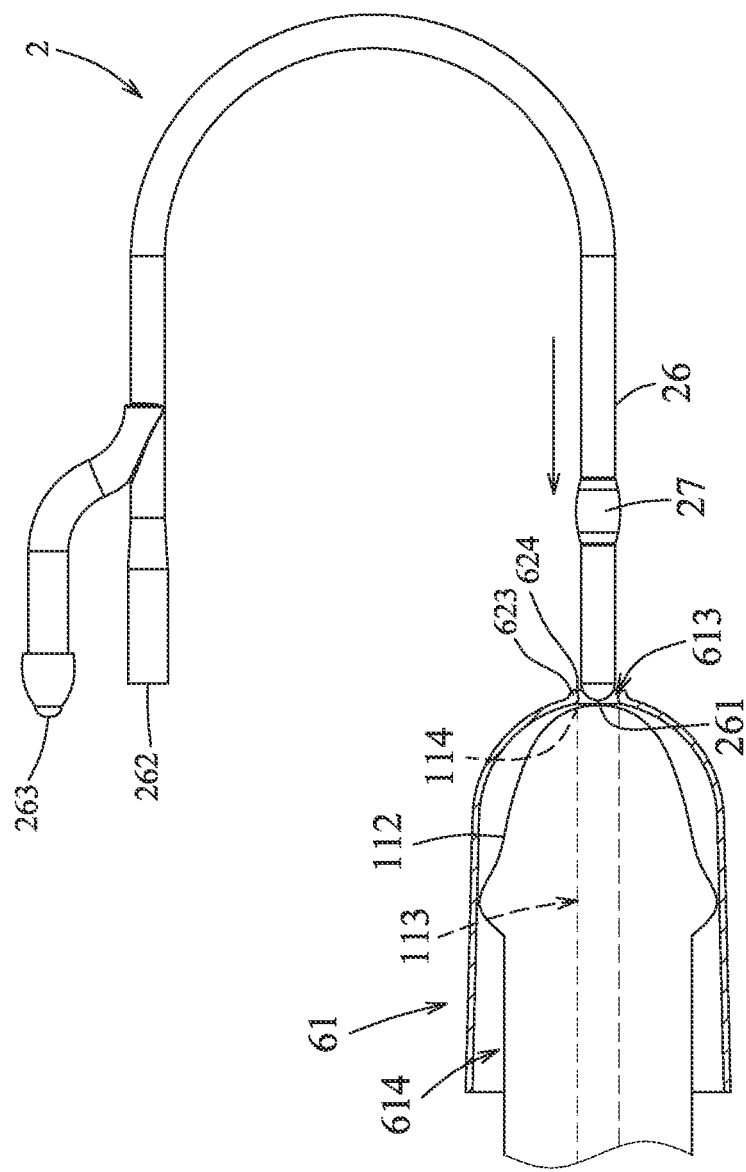
FIG. 20 is a schematic view illustrating a sleeve assembly of the fifth embodiment being assembled with a urinary catheter of the fifth embodiment.

Referring to FIG. 20 in combination with FIG. 19, to carry out step S5, the inserting end 261 of the urinary catheter 2 is first aligned with the guiding hole 613 of the sleeve member 61 and then is inserted into the guiding hole 613. If the inserting end 261 deviates from a correct position and comes into contact with the chamfered surface 624 of the protruding ring 623, the inserting end 261 will slide along the chamfered surface 624 so that the inserting direction of the inserting end 261 is corrected by guidance of the chamfered surface 624. Therefore, even if the inserting end 261 encounters positional deviation, it can still be properly inserted into the guiding hole 613 via the chamfered surface 624, which provides conveniences in inserting the inserting end 261 into the guiding hole 613. After the inserting end 261 is inserted into the guiding hole 613, the tube body 26 of the urinary catheter 2 is bent into a configuration as shown in FIG. 20, in which both of the rear end 262 and the inserting end 261 are directed forwardly.

Figure 21:
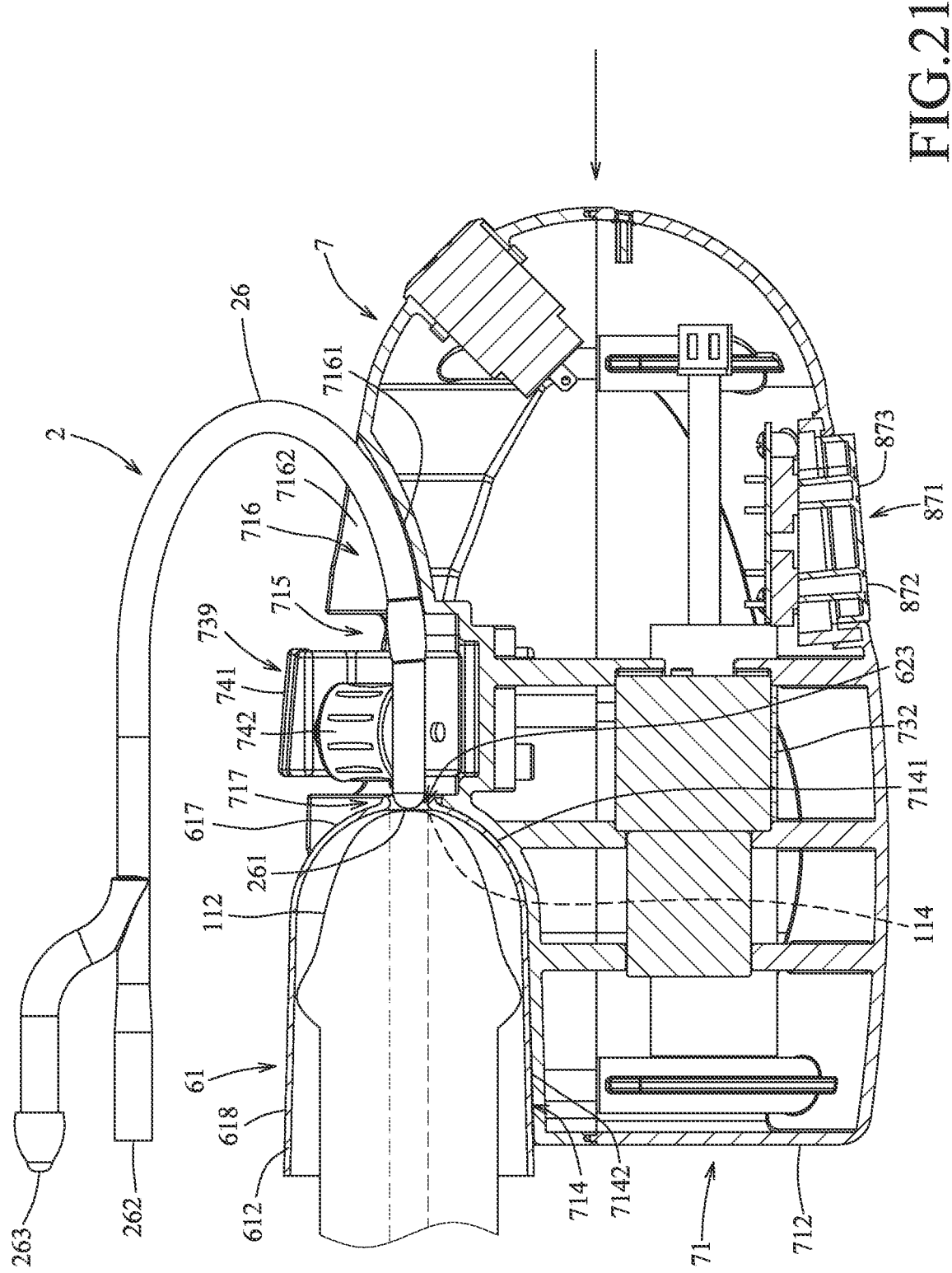
FIG. 21 is a schematic view illustrating a convey assembly of the fifth embodiment being assembled with the sleeve assembly and the urinary catheter of the fifth embodiment.

Referring further to FIG. 21, in executing step S6 that is subsequent to S5, the casing 71 is subsequently mounted to the sleeve member 61 such that the conveying mechanism 73 that is disposed in the casing 71 clamps the urinary catheter 2. Specifically, the frame 741 is pushed in a first pushing direction (F1) (see FIG. 18) by a user to rotate from the first position to the second position. Because the driven conveyor wheel 742 is distal from the driving conveyor wheel 738 when the frame 741 is in the second position, the urinary catheter 2 is allowed to move past the driven conveyor wheel 742 and the driving conveyor wheel 738 so as to reach the first casing passage 716 during the operation to carry out step S6 which will detailed hereinafter.

After the frame 741 is rotated to the second position, the positioning groove 714 and the second casing passage 717 are respectively aligned with the sleeve member 61 and the tube body 26 of the urinary catheter 2 in a front-rear direction (see FIG. 16). Then, the casing 71 is moved forwardly relative to the sleeve member 61 and the urinary catheter 2 in a direction toward said sleeve member 61. During the movement of the casing 71, the urinary catheter 2 sequentially enters the positioning groove 714, the second casing passage 717, a gap between the driven conveyor wheel 742 and the driving conveyor wheel 738, the accommodating space 715 and the first casing passage 716 until the urinary catheter 2 is positioned at the accommodating space 715 and the first casing passage 716. When the first curved positioning surface 7141 and the second curved positioning surface 7142 respectively abut against the outer dome-shaped surface 617 and the outer surrounding surface 618, the casing 71 is restrained to move forwardly relative to the sleeve member 61. At this time, the casing 71 is mounted to the sleeve member 61 and the urinary catheter 2. When the casing 71 is mounted to the sleeve member 61, the tubular wall portion 612 and the dome-shaped cap portion 611 are positioned in the positioning groove 714, and the protruding ring 623 is positioned in the second guiding groove 717. By virtue of the curved supporting surface 7161 supporting the tube body 26 of the urinary catheter 2 and by virtue of the restraining surfaces 7162 restraining the movement of the tube body 26 of the urinary catheter 2 in the direction transverse to the tube body 26, the urinary catheter 2 is kept in the bent shape as shown in FIG. 21.

Figure 22:
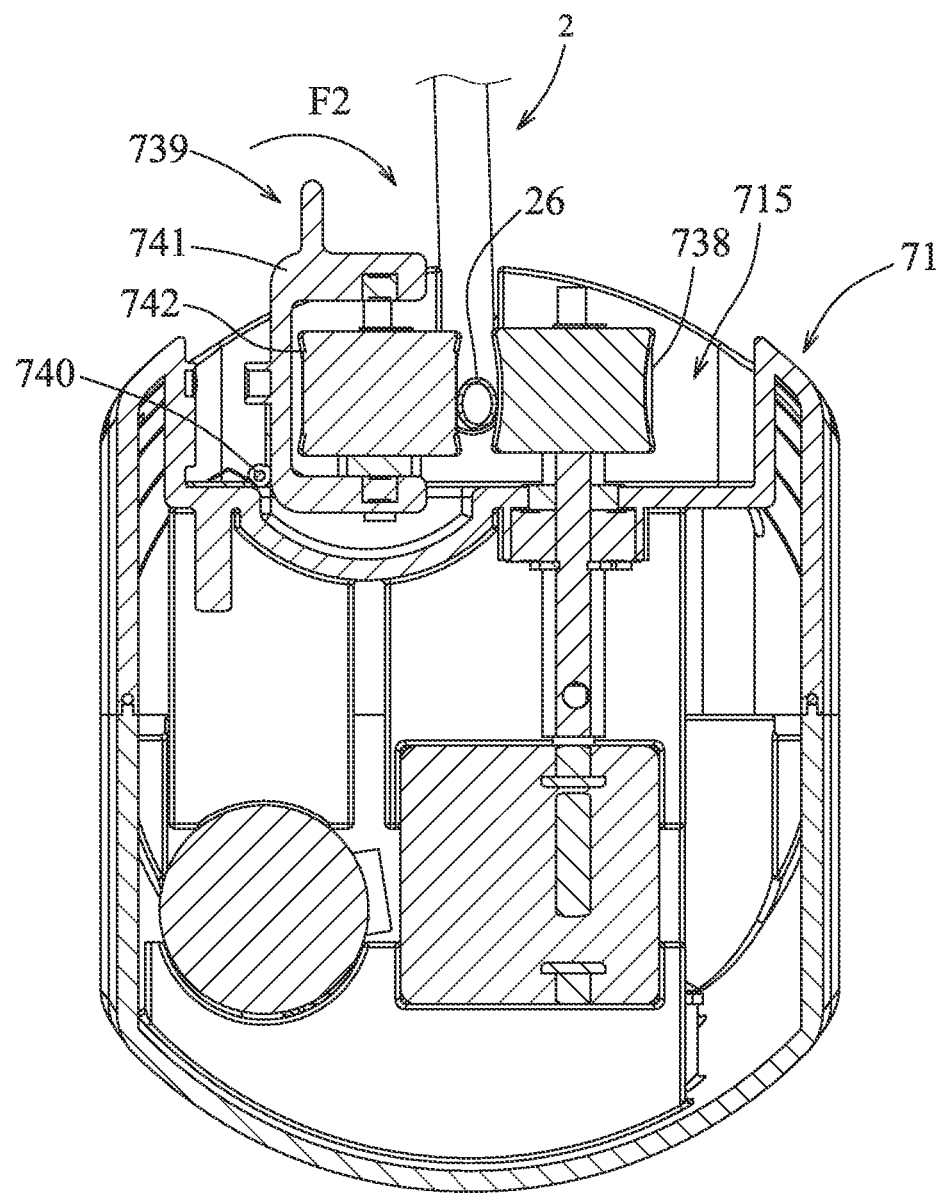
FIG. 22 is a view similar to FIG. 17, but illustrating a driven conveyor wheel and a driving conveyor wheel of the fifth embodiment cooperatively clamping the urinary catheter of the fifth embodiment.

Referring further to FIG. 22, afterwards, the frame 741 is pushed in a second pushing direction (F2) opposite to the first pushing direction (F1) by the user to rotate from the second position to the first position. When the frame 741 is in the first position, the driven conveyor wheel 742 cooperates with the driving conveyor wheel 738 to clamp the urinary catheter 2.

Figure 23:
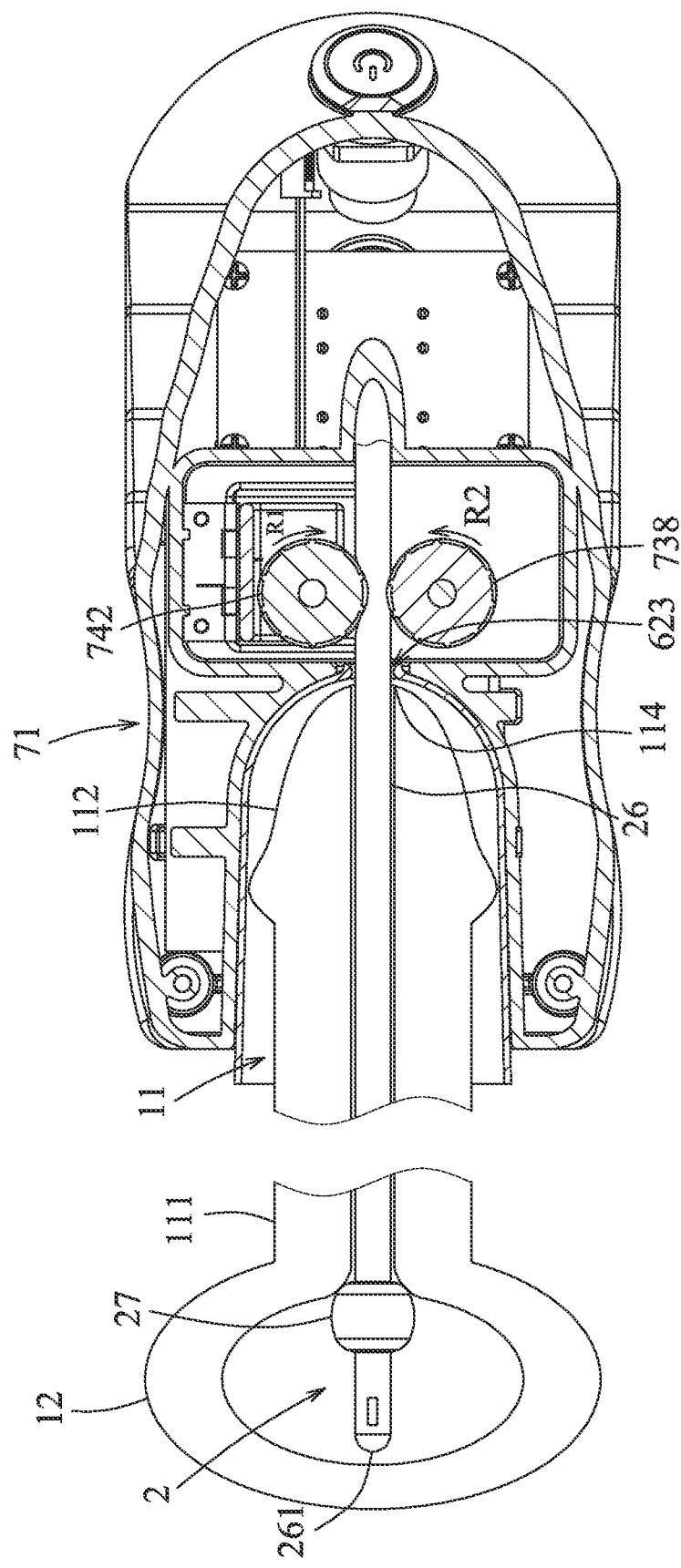
FIG. 23 is a fragmentary schematic view illustrating the urinary catheter of the fifth embodiment being inserted into the bladder.

Referring further to FIG. 23, in executing step S4, when a user presses the forward movement press portion 872 of the operation button 871 to switch the conveying assembly 7 into the forward conveying state, the motor 732 urges the driving conveyor wheel 738 to rotate in the second rotating direction (R2). Because the driving conveyor wheel 738 and the driven conveyor wheel 742 cooperatively clamp the urinary catheter 2, when the driving conveyor wheel 738 rotates in the second rotating direction (R2), the urinary catheter 2 is advanced forward, and the driven conveyor wheel 742 is caused to move by the advancing urinary catheter 2 to rotate in the first rotating direction (R1). Afterwards, when the inserting end 261 and the balloon body 27 of the urinary catheter 2 have been inserted into the bladder 12, the fluid is injected via the syringe into the syringe connection end 263 of the urinary catheter 2. Then, the fluid flows through the tube body 26 into the balloon body 27 and causes the balloon body 27 to expand. Consequently, the urinary catheter 2 is held in the bladder 12 via the fluid-filled balloon body 12 thereof.

Afterwards, the conveying assembly 7 is removed from the sleeve assembly 6 and the urinary catheter 2. Specifically, the frame 741 is pushed in the first pushing direction (E1) (see FIG. 18) to rotate again to the second position so that the frame 741 is away from the urinary catheter 2. Then, the casing 71 is moved rearwardly to a suitable distance to separate the positioning groove 714 from the sleeve member 61 and to separate the urinary catheter 2 from the accommodating space 715 and the first casing passage 716. As the conveying assembly 7 moves rearwardly, the urinary catheter 2 sequentially leaves the first casing passage 716, the accommodating space 715, the gap between the driven conveyor wheel 742 and the driving conveyor wheel 738, the second casing passage 717 and the positioning groove 714. Consequently, the conveying assembly 7 is removed from the sleeve assembly 6 and the urinary catheter 2. Since the conveying assembly 7 is removed from the urine catheter 2, discomfort that may be caused to a patient by the weight of the conveying assembly 7 during drainage of urine through the urinary catheter 2 is avoided.

It is noted that the accommodating space 715 and the first casing passage 716 are adapted to positon the urine catheter 2 when the sleeve member 61 assembled with the urine catheter 2 is positioned in the positioning groove 714. The positioning groove 714 and the second casing passage 717 are configured in such a manner that the urine catheter 2 assembled with the sleeve member 61 is allowed to move past the positioning groove 714 and the second casing passage 717 for being placed into or removed away from the accommodating space 715 and the first casing passage 716.

By virtue of the positioning groove 714, the accommodating space 715, the first casing passage 716 and the second casing passage 717, all of which are recessed at the top surface 724 to be opened at the top surface 724, and by virtue of the pressing unit 739 being movably connected the casing 71 and being operable to move towards or away from the driving conveyor wheel 738, the casing 71 can be assembled with or removed from the urinary catheter 2 without much effort.

To remove the urinary catheter 2 from the bladder 12 and the penis 11, a user has to drain the fluid in the balloon body 27 through the syringe connection end 263 of the urinary catheter 2. Next, the conveying assembly 7 is reassembled with the sleeve assembly 6 and the urinary catheter 2 as described herebefore. Afterwards, the rearward movement press portion 873 is pressed so that the conveying assembly 7 is switched to the rearward conveying state. At this time, the driving conveyor wheel 738 and the driven conveyor wheel 742 cooperatively clamp the urinary catheter 2, and the motor 732 urges the driving conveyor wheel 738 to rotate in the first rotating direction (R1) so that the urinary catheter 2 is moved rearward. Consequently, the inserting end 261 of the urinary catheter 2 is sequentially removed from the bladder 12, the urethra 113, and the external urethral orifice 114.

In summary, by virtue of the controller 8 controlling the conveying assembly 7 to advance the urinary catheter 2 to the guiding hole 613 of the sleeve member 61 through the first and second casing passages 716, 717, the urinary catheter 2, which is flexible, can be held straight and inserted precisely into the external urethral orifice 114 through the guiding hole 613. This can reduce the risk of causing discomfort to a patient due to the operation of an operator having limited experiences and training.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A urinary catheter conveying device adapted for guiding a urinary catheter to a penis, said urinary catheter conveying device comprising:
    a sleeve assembly adapted to be disposed on the penis, and including a sleeve member that is adapted for sleeving onto a glans of the penis and that has a guiding hole adapted to be registered with an external urethral orifice of the glans;
    a conveying assembly including
        a casing that is removably mounted to said sleeve member, and
        a conveying mechanism that is disposed in said casing, and that is adapted for advancing the urinary catheter to said guiding hole such that the urinary catheter is inserted into the external urethral orifice through said guiding hole; and
    a controller electrically coupled to said conveying mechanism and adapted for controlling said conveying mechanism to advance the urinary catheter to said guiding hole;
    wherein said casing of said conveying assembly has a front surface, a top surface, and a positioning groove to receive and position said sleeve member, said positioning groove being recessed in said front surface and said top surface;
    wherein said top surface of said casing is recessed to form an accommodating space that accommodates said conveying mechanism, a first casing passage that spatially communicates with a rear side of said accommodating space opposite to said positioning groove, and a second casing passage that is located between said positioning groove and said accommodating space, and that is opposite to said first casing passage;
    wherein said accommodating space and said first casing passage are adapted to position the urinary catheter when said sleeve member assembled with the urinary catheter is positioned in said positioning groove; and
    wherein said positioning groove and said second casing passage are configured in such a manner that the urinary catheter assembled with said sleeve member is allowed to move past said positioning groove and said second casing passage for being placed into or removed away from said accommodating space and said first casing passage.

2. The urinary catheter conveying device as claimed in claim 1, wherein said sleeve member includes
    a dome-shaped cap portion, and a tubular portion that extends from one end of said dome-shaped cap portion, said guiding hole extending centrally through said dome-shaped cap portion, a cross section of said guiding hole corresponding in shape to a cross section of the urinary catheter, said tubular portion and said dome-shaped cap portion cooperatively defining an accommodating groove that spatially communicates with said guiding hole and that is adapted for accommodating the glans.

3. The urinary catheter conveying device as claimed in claim 1, wherein:
    said first casing passage is adapted for directing the urinary catheter to extend through said accommodating space; and
    said second casing passage spatially communicates with a front side of said accommodating space and said positioning groove, is aligned with said guiding hole, and is adapted for directing the urinary catheter to extend through said guiding hole of said sleeve member.

4. The urinary catheter conveying device as claimed in claim 1, wherein:
    each of said sleeve assembly and said conveying assembly is configured to be portable;

said conveying mechanism includes a wireless communication unit and a rechargeable battery; and said controller is configured to be portable, and is wirelessly and electrically coupled to said wireless communication unit.

5. The urinary catheter conveying device as claimed in claim 1, wherein:
said conveying mechanism of said conveying assembly includes
a motor that is disposed on said casing,
a driving conveyor wheel that is located in said accommodating space and that is connected to said motor, and
a pressing unit that is located in said accommodating space, that is movably connected to said casing, that is spaced apart from said driving conveyor wheel, and that is operable to move towards or away from said driving conveyor wheel so as to clamp the urinary catheter against said driving conveyor wheel or unclamp the urinary catheter.

6. The urinary catheter conveying device as claimed in claim 5, wherein:
said pressing unit includes
a hinge that is connected to said casing,
a frame that is mounted to said hinge and that is rotatable relative to said casing via said hinge, and
a driven conveyor wheel that is rotatably mounted to said frame and that is co-movable with said frame relative to said casing;
said frame is operable to rotate relative to said casing between a first position and a second position;
when said frame is in the first position, said driven conveyor wheel is proximate to said driving conveyor wheel and cooperates with said driving conveyor wheel to clamp the urinary catheter; and
when said frame is in the second position, said driven conveyor wheel is in an inclining position, is distal from said driving conveyor wheel and unclamps the urinary catheter.

7. The urinary catheter conveying device as claimed in claim 1, wherein:
said sleeve member is made from a resilient material and includes
a tubular portion,
a dome-shaped cap portion that is connected to one end of said tubular portion, and
a protruding ring that extends centrally through and protrudes from said dome-shaped portion opposite to said tubular portion, that defines said guiding hole, and that has a chamfered surface surrounding said guiding hole, said chamfered surface being adapted for directing the urinary catheter to extend into said guiding hole when contacting with the urinary catheter; and
when said casing is mounted to said sleeve member, said tubular wall portion and said dome-shaped cap portion are positioned in said positioning groove of said casing, and said protruding ring is positioned in said second guiding groove.

8. The urinary catheter conveying device as claimed in claim 1, wherein said casing further has a curved supporting surface that extends from said top surface of said casing to said accommodating space and that is adapted for supporting the urinary catheter, and two restraining surfaces that are respectively connected to two sides of said curved supporting surface which are opposite to one another in a direction transverse to an extending direction of said curved supporting surface, that cooperate with said curved supporting surface to define said first casing passage, and that are adapted for restraining movement of the urinary catheter in a direction transverse to the urinary catheter.

9. A urinary catheterization system comprising:
a urinary catheter; and
the urinary catheter conveying device of claim 1.

10. The urinary catheterization system as claimed in claim 9, wherein:
said urinary catheter has an inserting end that is adapted to be inserted into the external urethral orifice of the glans;
said urinary catheterization system further comprises a pressure sensor that is mounted to said urinary catheter adjacent to said inserting end of said urinary catheter, that generates a first pressure signal when detecting a pressure whose value is larger than a preset value, and that generates a second pressure signal when detecting that a first detected state, in which a pressure is detected, is switched into a second detected state, in which no pressure is detected; and
said conveying mechanism of said conveying assembly is electrically coupled to said pressure sensor and ceases to advance said urinary catheter when receiving one of the first and second pressure signals from said pressure sensor.

11. A method of using the urinary catheterization system of claim 9, comprising steps of:
a) assembling said sleeve assembly of said urinary catheter conveying device onto a penis;
b) assembling said sleeve assembly with said conveying assembly of said urinary catheter conveying device and said urinary catheter; and
c) controlling said conveying assembly to advance said urinary catheter to said guiding hole of said sleeve member of said sleeve assembly by said controller of said urinary catheter conveying device so that said urinary catheter is inserted into an external urethral orifice of a glans of said penis through said guiding hole.

12. The method as claimed in claim 11, wherein
said sleeve assembly is assembled with the conveying assembly and the urinary catheter through the steps of inserting said urinary catheter into said guiding hole of said sleeve member beforehand, and
subsequently mounting said casing of said conveying assembly of said urinary catheter conveying device to said sleeve member of said sleeve assembly and said urinary catheter such that said conveying mechanism of said urinary catheter conveying device that is disposed in said casing clamps said urinary catheter.

13. A urinary catheter conveying device adapted for guiding a urinary catheter to a penis, said urinary catheter conveying device comprising:
a sleeve assembly adapted to be disposed on the penis, and including a sleeve member that is adapted for sleeving onto a glans of the penis and that has a guiding hole adapted to be registered with an external urethral orifice of the glans;
a conveying assembly including
a casing that is removably mounted to said sleeve member, and
a conveying mechanism that is disposed in said casing, and that is adapted for advancing the urinary catheter to said guiding hole such that the urinary catheter is inserted into the external urethral orifice through said guiding hole; and a controller electrically coupled to said conveying mechanism and adapted for controlling said conveying mechanism to advance the urinary catheter to said guiding hole;
wherein said casing has
- a positioning groove to receive and position said sleeve member,
- an accommodating space that accommodates said conveying mechanism and that has two opposite ends,
- a first casing passage that spatially communicates with one of said opposite ends of said accommodating space, and that is adapted for directing the urinary catheter to extend through said accommodating space, and
- a second casing passage that spatially communicates with the other one of said opposite ends of said accommodating space and said positioning groove, that is aligned with said guiding hole, and that is adapted for directing the urinary catheter to extend through said guiding hole of said sleeve member.

* * * * *